United States Patent
Moran et al.

(10) Patent No.: US 8,835,105 B2
(45) Date of Patent: *Sep. 16, 2014

(54) SPERM-SPECIFIC CATION CHANNEL, CATSPER4, AND USES THEREFOR

(75) Inventors: Magdalene M. Moran, Brookline, MA (US); Jayhong A. Chong, Brookline, MA (US); Ian S. Ramsey, Boston, MA (US); David Clapham, Wellesley, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/371,033

(22) Filed: Feb. 10, 2012

(65) Prior Publication Data

US 2013/0067603 A1   Mar. 14, 2013

Related U.S. Application Data

(60) Continuation of application No. 12/244,630, filed on Oct. 2, 2008, now Pat. No. 8,137,918, which is a division of application No. 10/523,475, filed as application No. PCT/US03/24359 on Aug. 4, 2003, now abandoned.

(60) Provisional application No. 60/402,115, filed on Aug. 7, 2002.

(51) Int. Cl.
  *C12Q 1/00* (2006.01)
  *C12Q 1/68* (2006.01)
  *G01N 27/00* (2006.01)
  *C07K 14/00* (2006.01)

(52) U.S. Cl.
  USPC .............. 435/4; 435/6.1; 436/149; 530/350

(58) Field of Classification Search
  None
  See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 5,459,039 A | 10/1995 | Modrich et al. | |
| 5,498,531 A | 3/1996 | Jarrell | |
| 6,159,478 A | 12/2000 | Haanes et al. | |
| 6,787,309 B2 | 9/2004 | Splawski et al. | |
| 8,137,918 B2 * | 3/2012 | Moran et al. | 435/6.13 |
| 2001/0039335 A1 | 11/2001 | Jacobs et al. | |
| 2002/0082210 A1 | 6/2002 | Curtis | |

FOREIGN PATENT DOCUMENTS

| WO | WO-00/61624 | 10/2000 |
|---|---|---|
| WO | WO-00/66735 | 11/2000 |
| WO | WO-01/07611 | 2/2001 |
| WO | WO-01/54477 | 8/2001 |
| WO | WO-01/75067 | 10/2001 |
| WO | WO-01/88090 | 11/2001 |
| WO | WO-01/90304 | 11/2001 |
| WO | WO-02/090567 | 11/2002 |
| WO | WO-03/089583 | 10/2003 |
| WO | WO-03/091434 | 11/2003 |
| WO | WO-03/099865 | 12/2003 |

OTHER PUBLICATIONS

Arnoult, et al., "Activation of mouse sperm T-type Ca2+ channels by adhesion to the egg zona pellucida," Proc. Natl. Acad. Sci. USA, vol. 93, pp. 13004-13009, 1996.
Avidan et al., "Catsper2, a human autosomal nonsyndromic male infertility gene," European Journal of Human Genetics, 2003, 11:497-502.
Bedford, J.M., "Mammalian Fertilization Misread? Sperm Penetration of the Eutherian Zona Pellucida Is Unlikely to be a Lytic Event," Biology of Reproduction, vol. 59, pp. 1275-1287, 1998.
Chan H.C., Cation and anion channels in rat and human spermatozoa, Biochimica et Biophysica Acta, vol. 1323; pp. 117-129 (1997).
Colman, P.M., "Effects of amino acid sequence changes on antibody-antigen interactions," Research in Immunology, vol. 145; pp. 33-36 (1994).
Darszon, et al., "Ion Channels in Sperm Physiology," Physiological Reviews, vol. 79, No. 2, Apr. 1999, pp. 481-510.
Database EMBL, Oct. 11, 2001, XP002314905, Database Accession No. AAS90759, 2 pages.
Database EMBL, Sep. 11, 1997, XP002314902, Database Accession No. AA574312.
Database EMBL, Nov. 14, 1997, XP002314900, Database Accession No. AA662668, 2 pages.
Database EMBL, Dec. 2, 2000, XP002314901, Database Accession No. BF436942, 2 pages.
Database EMBL, Mar. 2, 2000, XP002314904, Database Accession No. AW472972, 2 pages.
Database EMBL, Oct. 20, 2000, XP002314898, Database Accession No. BF092492, 2 pages.

(Continued)

*Primary Examiner* — Ruixang Li
(74) *Attorney, Agent, or Firm* — Wilmer Cutler Pickering Hale and Dorr LLP

(57) ABSTRACT

Nucleic acid and protein sequences relating to a cation channel which is sperm-specific (CatSper4) are disclosed. The CatSper4 protein is shown to be specifically expressed in sperm. Nucleic acids, vectors, transformed cells, transgenic animals, polypeptides, and antibodies relating to the CatSper4 gene and protein are disclosed. Also provided are methods of in vitro fertilization and contraception, methods of identifying modulators of CatSper4 activity, methods of genotyping subjects with respect to CatSper4, and methods of diagnosing and treating CatSper4-mediated disorders, including infertility. Related business methods are also disclosed.

11 Claims, 2 Drawing Sheets

(56) References Cited

OTHER PUBLICATIONS

Database EMBL, Jan. 25, 2001, XP002314968, Database Accession No. BF934163, 2 pages.
Database EMBL, Mar. 25, 2004, XP002314912, Database Accession No. ACN41330, 2 pages.
Database EMBL, Nov. 29, 2001, XP002314910, Database Accession No. ABL90376, 2 pages.
Database EMBL, Nov. 29, 2001, XP002314911, Database Accession No. ABB89967, 2 pages.
Database EMBL, Nov. 30, 1999, XP002314903, Database Accession No. AW197851, 2 pages.
Database EMBL, Jun. 8, 2000, XP002314899, Database Accession No. AW971983, 2 pages.
Database EMBL, Oct. 8, 2001, XP002314906, Database Accession No. BI826910, 2 pages.
Database EMBL, Oct. 8, 2001, XP002314907, Database Accession No. BI829451, 2 pages.
Database EMBL, May 9, 2001, XP002314908, Database Accession No. BG718343, 2 pages.
Database EMBL, Dec. 1, 2001, XP002306737, Database Accession No. Q96P76, 2 pages.
Database EMBL, Dec. 1, 2001, XP002306739, Database Accession No. Q91ZR5, 2 pages.
Database EMBL, Mar. 3, 2000, XP002306735, Database Accession No. AA416682, 2 pages.
Database EMBL, Mar. 3, 2000, XP002306736, Database Accession No. AA416577, 2 pages.
Database EMBL, May 30, 2000, XP002306734, Database Accession No. AP000586, 2 pages.
Database EMBL, May 9, 2001, XP002314909, Database Accession No. BG718245, 2 pages.
Database EMBL, Oct. 15, 2001, XP002306738, Database Accession No. AF407333, 2 pages.
Database EMBL, Oct. 15, 2001, XP002306740, Database Accession No. AF407332, 2 pages.
Garbers D.L., "Ion channels. Swimming with sperm," Nature, vol. 413, No. 6856, Oct. 2001, pp. 579, 581-582, XP 002314956.
Hillier et al., (1997) Accession No. AA416577.1. Accessed Oct. 29, 2010 at HTTp://www.nbci.nlm.nih.gov./nucest/AA416577.1?report=gbwithparts&log$=seqview. 2 pages.
Hillier et al., Accession No. AA41682.1 (1997).
Hyne and Garbers, "Calcium-dependent increase in adenosine 3', 5'-monophosphate and induction of the acrosome reaction in guinea pig spermatozoa," Proc. Natl. Acad. Sci. USA, vol. 76, No. 11, pp. 5699-5703, 1997.
Jin et al., "Catsper3 and Catsper4 encode two cation channel-like proteins exclusively expressedmin the testis," Biology of Reproduction, vol. 73, pp. 1235-1242 (2005).
Jungnickel, et al., "Trp2 regulates entry of Ca2+ into mouse sperm triggered by egg ZP3," Nature Cell Biology, vol. 3, May 2001, pp. 499-502.
Lehmann-Horn et al., "Voltage-Gated Ion Channels and hereditary disease," Physiol Rev, vol. 79(4), pp. 1317-1372 (1999).
Lobley et al., "Identification of human and mouse CatSper3 and Catspem4 genes: Characterisation of a common interaction domain and evidence for expression in testis," Reprod. Biol. Endocrinol. 2003, Aug. 1, 1:53, 15 pages.
Martelange et al., "Identification on a Human Sarcoma of two new genes with tumor-specific expression," Cancer Research, vol. 60, pp. 3848-3855 (2000).
N.A., Suppl. 1, Trends Pharmacol Sci, vol. 18, pp. 77-84 (1997).
Nikpoor et al., "CatSper gene expression in postnatal development of mouse testis and in subfertile men deficient sperm motility," human Reprod. vol. 19(1); pp. 124-128 (2004).
O'Toole, et al., "Ca2+ Entry through Store-operated Channels in Mouse Sperm Is Initiated by Egg ZP3 and Drives the Acrosome Reaction," Molecular Biology of the Cell, vol. 11, pp. 1571-1584, May 2000.
Quill, et al., "A voltage-gated ion channel expressed specifically in spermatozoa," PNAS, vol. 98, No. 22, 12527-12531, 2001.
Ren et al., A Sperm Ion Channel Required for Sperm Motility and Male Fertility, Nature, Macmillian Journals Ltd., London, vol. 413, No. 6856, Oct. 11, 2001, pp. 603-609.
Sanger Centre, "Genome Sequence of the Nematode C. elegans: A Platform for investigating Biology," Science, vol. 282, pp. 2012-2018 (1998).
Santi, et al., "A dihydropyridine-sensitive T-type Ca2+ current is the main Ca2+ current carrier in mouse primary spermatocytes," American Journal of Physiology, vol. 271, pp. C1583-C1593, 1996.
Serrano, et al., "Voltage-dependent Ca2+ channel subunit expression and immunolocalization in mouse spermatogenic cells and sperm," FEBS Letters, 462, pp. 171-176, 1999.
Skolnick et al., "From genes to protein structure and function: novel applications of computational approaches in the genomic era," Trends in Biotechnology, 2000, 18:34-39.
Strausberg, R., Homo Sapiens, Clone Image. Mar. 3, 2003, pp. 1-3, especially pp. 2-3.
Strausberg, Robert. "wq62d12.x1 NCI_CGAP_GC6 Homo Sapiens CDNA close IMAGE:2475863 3-, mRNA sequence." [online] No Month Listed 1999. [retrieved Sep. 3, 2011] Retrieved from the Internet: <URL:htto://www.ncbi.nim.nih.gov/nucest/AW003002.1> pp. 1-2.
Tash, Joseph S., "Role of the Camp, Calcium, and Protein Phosporylation in Sperm Motility," Controls of Sperm Motility: Biological and Clinical Aspects, eds. Gagnon, pp. 229-240, 1990.
Wassarman, et al., "A profile of fertilization in mammals," Nature Cell Biology, vol. 3, E59-E64, Feb. 2001.
Watson et al., Recombinant DNA, 2nd Edition, W.H. Freeman and Company, p. 107, (1992).
Wennemuth, et al., "Cav2.2 and Cav2.3 (N- and R-type) Ca2+ Channels in Depolarization-evoked Entry of Ca2+ into Mouse Sperm," The Journal of Biological Chemistry, vol. 275, No. 28, pp. 21210-21217, 2000.
Weyand, et al., "Cloning and functional expression of a cyclic nucleotide-gated channel from mammalian sperm," Nature, vol. 368, pp. 859-863, Apr. 28, 1994.
Whisstock et al., "Prediction of protein function from protein sequence and structure," Quarterly Review of Biophysics, 2003, 36:307-340.
Wiesner, et al., "Cyclic Nucleotide-gated Channels on the Flagellum Control of Ca2+ Entry into Sperm," The Journal of Cell Biology, vol. 142, No. 2, pp. 473-484, 1998.
Yanigimachi, R. "Mammalian Fertilization," The Physiology of Reproduction, Second Edition, eds. Knobil and Neill, pp. 189-317, 1994.

\* cited by examiner

FIGURE 1

MSQHFHHNPV RVKSGSLFAT ASEALQARLS KIKRKDKECQ AYFRKVI<u>KST</u>  0050 <u>FFQIVMITTV</u>
<u>TTNSFLLVLG TNYDIQFEFF RTFEVSELFF VSVYVCEFLM</u>  0100
<u>KVYVDPITYW KDGYNILDVI ILIILTIPYL LRKIKGNHSA</u> YLHFADGIQS  0150
LRILK<u>LISYS RGIRTLIIAV GETVYTVASV LTLLFLLMFV FAILGFCLFG</u>  0200
VTDRGDLENW GNLASAFFTL <u>FSLATVDGWT D</u>LQEELDKRK FTVS<u>RAFTIL</u>  0250 <u>FILLASFIFL</u>
<u>NMFVGVMIMH TED</u>SMKKFER DLTLERNLAI MEEKQIILKR  0300 QQEEVNRLMN TQKTGSMNFI
DMVEGFKKTL RHTDPMVLDD FSTSLSFIDI  0350 YLVTLDNQDV IVSKLQELYC EIVNVLSLML
EDMPKESSSS LSGLS  0395

FIGURE 2

MSQHRHQRHS RVISSSPVDT TSVGFCPTFK KFKRNDDECR AFVKR<u>VIMSR</u>  0050
<u>FFKIIMISTV TSNAFFMALW TSYDIRYRLF RLLEFSEIFF VSICTSELSM</u>  0100
KVYVDPI<u>NYW KNGYNLLDVI IIIVMFLPYA LRQLMGKQFT</u> YLYIADGMQS  0150 LRILK<u>LIGYS</u>
<u>QGIRTLITAV GQTVYTVASV LLLLFLLMYI FAILGFCLFG</u>  0200
SPDNGDHD<u>NW GNLAAAFFTL FSLATVDGWT D</u>LQKQLDNRE FA<u>LSRAFTII</u>  0250 <u>FILLASFIFL</u>
<u>NMFVGVMIMH TED</u>SIRKFER ELMLEQQEML MGEKQVILQR  0300 QQEEISRLMH IQKNADCTSF
SELVENFKKT LSHTDPMVLD DFGTSLPFID  0350
IYFSTLDYQD TTVHKLQELY YEIVHVLSLM LEDLPQEKPQ SLEKVDEK  0398

FIGURE 3

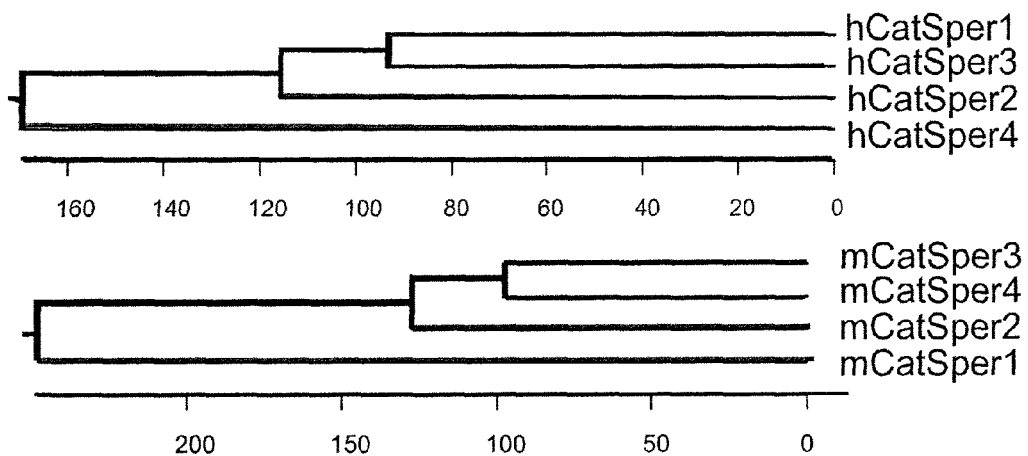

hCatSper3 and hCatSper1 are 21% identical
hCatSper3 and hCatSper2 are 22% identical
hCatSper4 and hCatSper1 are 17% identical
hCatSper4 and hCatSper2 are 21% identical mCatSper3 and mCatSper1 are 20% identical
mCatSper3 and mCatSper2 are 22% identical
mCatSper4 and mCarSper1 are 22% identical
mCatSper4 and mCatSper2 are 22% identical hCatSper1 and mCatSper1 are 48% identical
hCatSper2 and mCatSper2 are 71% identical
hCatSper3 and mCatSper3 are 68% identical
hCatSper4 and mCatSper4 are 65% identical

US 8,835,105 B2

SPERM-SPECIFIC CATION CHANNEL, CATSPER4, AND USES THEREFOR

RELATED APPLICATIONS

This application is a continuation of U.S. application Ser. No. 12/244,630, filed Oct. 2, 2008, which is a divisional application of U.S. application Ser. No. 10/523,475, filed Sep. 16, 2005, which claims benefit of priority to PCT International Application No. PCT/US2003/024359, filed Aug. 4, 2003 and U.S. Provisional Application Ser. No. 60/402,115, filed Aug. 7, 2002, the contents of which are incorporated by reference herein in their entirety.

SEQUENCE LISTING

The instant application contains a Sequence Listing which has been submitted in ASCII format via EFS-Web and is hereby incorporated by reference in its entirety.

BACKGROUND OF THE INVENTION

1. Field of the Invention

The present invention relates to the fields of molecular biology, and reproductive technology. In particular, the invention relates to a cation channel protein expressed specifically in sperm cells, to nucleic acids encoding the protein, cells engineered to express the protein, assays for compounds affecting the activity of the protein, and to the use of such compounds in the treatment or causation of infertility, or as a means of contraception or animal control.

2. Description of the Related Art

Sperm and ova reciprocally interact in mammalian fertilization (Wassarman, et al. (2001), *Nature Cell Biology* 3, E59-E64; Yanagimachi (1994), in *The Physiology of Reproduction*, eds. Knobil & Neill (Raven Press, New York), pp. 189-315). To reach the site of fertilization, sperm must travel relatively long distances and become primed for fertilization of the ova through capacitation and other processes. Once they arrive at the surface of an ovum, sperm interact with ovum extracellular matrix glycoproteins including the zona pellucida proteins. Sperm release acidic material during the acrosome reaction, a signaling event which presumably involves the opening of $Ca^{2+}$ channels and the influx of $Ca^{2+}$ into the sperm heads (O'Toole, et al. (2000), *Mol Biol Cell* 11, 1571-84). The TRPC2 protein, a putative $Ca^{2+}$-permeant channel, has recently been implicated in the acrosome reaction (Jungnickel, et al. (2001), *Nat Cell Biol* 3, 499-502). Penetration of sperm through the thick outer layer of the ovum is achieved through chemical lysis of the ovum coat and/or the mechanical motion of sperm (Bedford (1998), *Biol Reprod* 59, 1275-87). Following infiltration of the ovum ZP coat, the sperm membrane fuses with that of ovum. Fusion is followed by activation of the fertilization process, beginning with $Ca^{2+}$ oscillations in the ovum (Wassarman, et al. (2001), *Nature Cell Biology* 3, E59-E64; Yanagimachi (1994), in *The Physiology of Reproduction*, eds. Knobil & Neill (Raven Press, New York), pp. 189-315).

$Ca^{2+}$ and cyclic nucleotides control sperm motility (Tash (1990) in *Controls of Sperm Motility: biological and clinical aspects*, ed. Gagnon (CRC Press, Boca Raton), pp. 229-240; Darszon, et al. (1999), *Physiol Rev* 79, 481-510; Hyne & Garbers (1979), *Proc Natl Acad Sci USA* 76, 5699-703) and several voltage-dependent $Ca^{2+}$ channel ($Ca_V$) mRNAs and cyclic nucleotide-gated (CNG) channel proteins have been detected in sperm cell precursors (Darszon, et al. (1999), *Physiol Rev* 79, 481-510; Serrano, et al. (1999), *FEBS Lett* 462, 171-6; Weyand, et al. (1994) *Nature* 368, 859-63; Wiesner, et al. (1998), *J Cell Biol* 142, 473-84). Furthermore, low voltage activated, dihydropyridine-sensitive "T-type" channels (Santi, et al. (1996), *Am J Physiol* 271, C1583-93; Arnoult, et al. (1996), *Proc Natl Acad Sci USA* 93, 13004-9) and pharmacologically defined N- and R-type currents have been measured in spermatogenic cells (Wennemuth, et al. (2000), *J Biol Chem* 275, 21210-7). But the role of these channels in spermatogenesis or mature sperm function is not known.

Two sperm-specific cation channels, designated CatSper1 and CatSper2, have previously been described (Ren et al. (2001), *Nature* 413:603-9; Quill et al. (2001), *Proc. Natl. Acad. Sci. (USA)* 98(22):12527-31). These proteins are the subject of U.S. Prov. Appln. Ser. No. 60/288,402, filed May 3, 2001, U.S. Prov. Appln. Ser. No. 60/327,167, filed Oct. 4, 2001, U.S. Prov. Appln. Ser. No. 60/345,324, filed Oct. 22, 2001, and PCT Intl. Appln. No. PCT/US02/13487, filed May 3, 2002,

SUMMARY OF THE INVENTION

In one aspect, the present invention provides isolated nucleic acids corresponding to all or a portion of a CatSper4 gene. In some embodiments, the isolated nucleic acids include a nucleotide sequence of at least 10, 12, 14, 16 or 18 consecutive nucleotides of SEQ ID NO: 1 or SEQ ID NO: 3, or a sequence complementary thereto. In other embodiments, the nucleic acids include nucleotide sequences encoding a CatSper4 protein, at least a transmembrane domain of a CatSper4 protein, at least an extracellular loop of a CatSper4 protein, at least a pore region of a CatSper4 protein, at least an epitope of a CatSper4 protein having high predicted antigenicity, or a sequence complementary thereto. In particular embodiments, the nucleic acids include a sequence of SEQ ID NO: 1; a sequence of SEQ ID NO: 3; a sequence encoding a polypeptide comprising residues 46-75, 86-98, 108-137, 155-202, 209-233 and 242-272 of SEQ ID NO: 2; a sequence encoding a polypeptide comprising residues 48-73, 81-111, 113-134, 156-204, 208-233 and 245-273 of SEQ ID NO: 4; a sequence encoding a polypeptide comprising residues 76-85, 138-154 and 234-242 of SEQ ID NO: 2; a sequence encoding a polypeptide comprising residues 74-80, 135-155 and 234-244 of SEQ ID NO 4; a sequence encoding a polypeptide comprising residues 222-231 of SEQ ID NO: 2; a sequence encoding a polypeptide comprising residues approximately residues 222-231 of SEQ ID NO: 4; a sequence encoding a polypeptide comprising a high predicted antigenicity epitope of SEQ ID NO: 2; a sequence encoding a polypeptide comprising a high predicted antigenicity epitope of SEQ ID NO: 4; and a sequence complementary thereto.

In another aspect, the invention provides isolated nucleic acids encoding polypeptide having at least 80%, 85%, 90%, or 95% amino acid sequence identity with a CatSper4 protein; at least a transmembrane domain of a CatSper4 protein; at least an extracellular loop of a CatSper4 protein; and at least a pore region of a CatSper4 protein. In some embodiments, the isolated nucleic acids encode a polypeptide having at least 80%, 85%, 90% or 95% amino acid sequence identity with a CatSper4 protein and having CatSper4 activity in a cell capable of expressing CatSper4 activity. In some embodiments, the isolated nucleic acids include a regulatory element having at least 80%, 85%, 90% or 95% nucleotide sequence identity to at least 100, 200, 300 or 400 consecutive nucleotides from SEQ ID NO: 5, and that is capable of promoting transcription of a coding sequence operably joined thereto in a mammalian cell in which a CatSper4 gene can be expressed.

In another aspect, the invention provides isolated nucleic acids that hybridize to at least a portion of a nucleic acid of SEQ ID NO: 1 or SEQ ID NO: 3 under conditions including a wash step of 1.0×SSC at 65° C., a wash step of 0.5×SSC, a wash step of 0.2×SSC, or a wash step of 0.1×SSC. In some embodiments, the isolated nucleic acids encode a polypeptide having CatSper4 activity.

In another aspect, the invention provides nucleic acid comprising a nucleotide sequence encoding a polypeptide having CatSper4 activity, and that hybridizes to at least a portion of a nucleic acid of SEQ ID NO: 1 or SEQ ID NO: 3 under conditions including a wash step of 1.0×SSC at 65° C., a wash step of 0.5×SSC, a wash step of 0.2×SSC, or a wash step of 0.1×SSC; and that is operably joined to a heterologous regulatory region such that the sequence is expressed. In another embodiment, the invention provides a nucleic acid comprising a nucleotide sequence encoding a polypeptide having at least 80%, 85%, 90% or 95% amino acid sequence identity with an amino acid sequence of SEQ ID NO: 2 or 4; and is operably joined to a heterologous regulatory region such that the sequence is expressed.

In another aspect, the invention provides a kit for detecting at least a portion of a CatSper4 nucleic acid. The kits can include any of the foregoing isolated nucleic acids of the invention, and a means for detecting the isolated nucleic acid. In some embodiments, the means for detecting the isolated nucleic acid includes a detectable label bound thereto and, in some embodiments, the means includes a labeled secondary nucleic acid which specifically hybridizes to the first isolated nucleic acid.

In another aspect, the invention provides vectors including any of the foregoing isolated nucleic acids of the invention. In some embodiments, the vector includes a genetic construct capable of expressing the nucleic acids of the invention. In some embodiments, the nucleic acids of the invention are operably joined to an exogenous regulatory region and, in some embodiments, the nucleic acids are operably joined to heterologous coding sequences to form a fusion vector. In some embodiments, the vector includes a CatSper4 regulatory region and, in some embodiments, the CatSper4 regulatory region is operably joined to a heterologous coding sequence.

In another aspect, the invention provides cells transformed with the foregoing nucleic acids of the invention, or a genetic construct capable of expressing a nucleic acid of the invention. In some embodiments, the nucleic acid of the invention is operably joined to heterologous coding sequences to encode a fusion protein. In some embodiments, the cells are bacterial cells, yeast cells, insect cells, nematode cells, amphibian cells, rodent cells, or human cells. In some embodiments, the cells are mammalian somatic cells, fetal cells, embryonic stem cells, zygotes, gametes, germ line cells and transgenic animal cells.

In another aspect, the invention provides non-human transgenic animals. In these aspects, a genetic construct has introduced a modification into a genome of the animal, or an ancestor of the animal, and the modification includes insertion of a nucleic acid encoding at least a fragment of a CatSper4 protein, inactivation of an endogenous CatSper4 gene, or insertion by homologous recombination of a reporter gene operably joined to CatSper4 regulatory elements. In some embodiments, the modification is insertion of nucleic acid encoding a CatSper4 protein, at least a transmembrane domain of a CatSper4 protein, at least an extracellular loop of a CatSper4 protein, at least a pore region of a CatSper4 protein, or at least an epitope of a CatSper4 protein having high predicted antigenicity. In some embodiments, the animals are rats, mice, hamsters, guinea pigs, rabbit, dogs, cats, goats, sheep, pigs, and non-human primates.

In another aspect, the invention provides substantially pure protein preparations including polypeptides selected from a CatSper4 protein; at least a transmembrane domain of a CatSper4 protein; at least an extracellular loop of a CatSper4 protein; at least a pore region of a CatSper4 protein; and at least an epitope of a CatSper4 protein having high predicted antigenicity. In particular embodiments, the polypeptide is selected from SEQ ID NO: 2; SEQ ID NO: 4; residues 46-75, 86-98, 108-137, 155-202, 209-233 and 242-272 of SEQ ID NO: 2; residues 48-73, 81-111, 113-134, 156-204, 208-233 and 245-273 of SEQ ID NO: 4; residues 76-85, 138-154 and 234-242 of SEQ ID NO: 2; residues 74-80, 135-155 and 234-244 of SEQ ID NO 4; residues 222-231 of SEQ ID NO: 2; residues 222-231 of SEQ ID NO: 4; a high predicted antigenicity epitope of SEQ ID NO: 2; and a high predicted antigenicity epitope of SEQ ID NO: 4.

In another aspect, the invention provides a substantially pure protein preparation including polypeptides having at least 80%, 85%, 90%, or 95% amino acid sequence identity with a CatSper4 protein; at least a transmembrane domain of a CatSper4 protein; at least an extracellular loop of a CatSper4 protein; or at least a pore region of a CatSper4 protein. In some embodiments, the substantially pure protein preparation includes a polypeptide having at least 80%, 85%, 90%, or 95% amino acid sequence identity with a CatSper4 protein and having CatSper4 activity in a cell capable of expressing CatSper4 activity.

In another aspect, the invention provides a substantially pure antibody preparation including an antibody raised against a CatSper4 epitope. In some embodiments, the epitope has high predicted antigenicity. In some embodiments, the epitope includes an amino acid sequence within a high predicted antigenicity epitope of SEQ ID NO: 2, and a high predicted antigenicity epitope of SEQ ID NO: 4. In some embodiments, the antibody is a monoclonal antibody. In some embodiments, antibody is an Fab fragment, an $F(ab')_2$ fragment, an Fv fragment, or a single-chain Fv fragment (scFv).

In another aspect, the invention provides a kit for detecting at least an epitope of a CatSper4 protein. The kits include an anti-CatSper4 antibody of the invention and a means for detecting said antibody. In some embodiments, the means for detecting said anti-CatSper4 antibody includes a detectable label bound thereto and, in some embodiments, the means for detecting said anti-CatSper4 antibody includes a labeled secondary antibody which specifically binds to the anti-CatSper4 antibody.

In another aspect, the invention provides methods of identifying potential modulators of CatSper4 activity. The methods include contacting a candidate compound with a cell expressing a CatSper4 protein; measuring an indicator of CatSper4 activity in the cell; determining whether the candidate compound caused an increase or decrease in the indicator relative to a reference level; and identifying the candidate compound as a potential modulator of CatSper4 activity if the increase or decrease is significant. In some embodiments, the indicator is an indicator of the level of mRNA encoding the CatSper4 protein, an indicator of the level of CatSper4 protein, an indicator of cation flux across a membrane of said cell, or an indicator of whole cell or channel currents of said cell. In some embodiments, the cell has been transformed with a genetic construct capable of expressing a CatSper4 protein. In some embodiments, the cell is a mature sperm cell and the indicator is a measure of sperm motility.

In another aspect, the invention provides methods of identifying a potential modulator of CatSper4 activity comprising contacting a candidate compound with at least a structural domain of a CatSper4 protein; measuring binding, if any, between the candidate compound and the CatSper4 moiety; and identifying the candidate compound as a potential modulator of CatSper4 activity if the binding is significant. In some embodiments, the CatSper4 moiety is a CatSper4 protein; at least a transmembrane domain of a CatSper4 protein; at least an extracellular loop of a CatSper4 protein; or at least a pore region of a CatSper4 protein.

In another aspect, the invention provides a method of decreasing the fertility of a male subject by administering a compound to the subject which decreases CatSper4 activity. In another aspect, the invention provides a method of causing reversible infertility in a male subject by administering to a compound to the subject which decreases CatSper4 activity. In another aspect, the invention provides a method of contraception in which a compound which decreases CatSper4 activity is administered to a male or female subject. In each of the foregoing embodiments, the compound can be in an injection, a transdermal patch, a bioerodable implant, a lubricant, a moisturizer, a foam, a jelly, or a sponge. If the subject is a female, the compound can be administered into at least one of the vagina, uterus or fallopian tubes. In each of the foregoing embodiments, the compound can be a nucleic acid which is antisense to at least a portion of a CatSper4 gene or an antibody to a CatSper4 protein, including an Fab fragment, an F(ab')$_2$ fragment, an Fv fragment, or an scFv fragment. In some embodiments, the subject is a mammal. In some embodiments, the subjects are humans, dogs, cats, cows, sheep, horses, mice, rats, raccoons, and gophers. In others embodiments, the subjects are fish, amphibians or insects. In related aspects, the invention provides for the use of a compound which decreases CatSper4 activity in the preparation of a medicament for decreasing the fertility of a male subject, or causing reversible infertility in a male subject, or in the preparation of a contraceptive for administration to a male or female. thus, the invention provides contraceptive preparations including compounds which decrease CatSper4 activity, including nucleic acids which are antisense to at least a portion of a CatSper4 gene and antibodies to a CatSper4 protein.

In another aspect, the invention provides method of diagnosing a CatSper4-related disorder in a mammal by determining the presence or absence of a mutation in a CatSper4 gene. In some embodiments, the presence or absence of differences between a determined nucleic acid or amino acid sequence and a reference sequence indicates the presence or absence of mutations in the CatSper4 gene. In some embodiments, the method includes contacting at least a fragment of the CatSper4 protein with an antibody known to bind to a CatSper4 protein in which a mutation is known to be present or absent and detecting binding between the antibody and the CatSper4 protein. In other embodiments, the method includes measuring an indicator of CatSper4 activity in a cell; and comparing the measured indicator to a reference level. The indicator can be an indicator of the level of mRNA encoding CatSper4 protein, an indicator of the level of CatSper4 protein, an indicator of cation flux across a membrane of said cell, or an indicator of whole cell or channel currents of said cell. In some embodiments, the disorder is CatSper4-related infertility. In another aspect, the invention provides methods of genotyping a subject with respect to a CatSper4 gene.

In another aspect, the invention provides a method of in vitro fertilization by sperm having decreased CatSper4 activity, decreased motility, or decreased ability to penetrate a zona pellucida, in which a zona pellucida is removed from at least one ovum; and the ovum is contacted with at least one of sperm.

In another aspect, a method of treating a subject characterized by infertility due to decreased CatSper4 activity is provided. The method includes transforming sperm or sperm progenitors of the subject with a genetic construct capable of expressing a CatSper4 protein and using transformed sperm of said subject to fertilize an ovum. Alternatively, the method includes administering a CatSper4 protein to sperm or sperm progenitors of the subject.

In another aspect, the invention provides methods of diagnosing an anti-CatSper4 antibody-mediated infertility caused by anti-CatSper4 antibodies present in a female urogenital tract is provided. In another aspect, methods of treating an anti-CatSper4 antibody-mediated infertility caused by anti-CatSper4 antibodies present in a female urogenital tract are provided.

In another aspect, the invention provides methods of conducting a drug discovery business including (a) identifying, by an assay of the invention, one or more agents which antagonize CatSper4 activity; (b) determining if an agent identified in step (a), or an analog thereof, inhibits at least one of sperm motility or egg penetrance; (c) conducting therapeutic profiling of an agent identified as an inhibitor in step (b) for efficacy and toxicity in one or more animal models; and (d) formulating a pharmaceutical preparation including one or more agents identified in step (c) as having an acceptable therapeutic profile. In some embodiments, the method further includes the step of establishing a system for distributing the pharmaceutical preparation for sale, and optionally including establishing a sales group for marketing the pharmaceutical preparation.

BRIEF DESCRIPTION OF THE DRAWINGS

The following drawings are illustrative of embodiments of the invention and are not meant to limit the scope of the invention.

FIG. 1 shows the primary structure of mouse CatSper4 protein. (a) Amino acid sequence; the 6 putative transmembrane domains are underlined and the pore region is in bold.

FIG. 2 shows the primary structure of human CatSper4 protein. (a) Amino acid sequence; the 6 putative transmembrane domains are underlined and the pore region is in bold.

FIG. 3 shows cladograms of the (a) murine and (b) human CatSper family.

DETAILED DESCRIPTION

The present invention depends, in part, upon the identification, isolation and characterization of a cation channel protein which is expressed in sperm cells, but not in other tissues tested, and which plays a significant role in the motility of sperm and their ability to fertilize ova. The protein has been designated CatSper4 to indicate that it is the fourth Cation channel which is Sperm-specific to be identified. Other members of the CatSper family of proteins include CatSper1 (Ren et al. (2001), *Nature* 413:603-9; U.S. Prov. Appln. Ser. No. 60/288,402, filed May 3, 2001; U.S. Prov. Appln. Ser. No. 60/327,167, filed Oct. 4, 2001; PCT Intl. Appln. No. PCT/US02/13487, filed May 3, 2002), CatSper2 (Quill et al. (2001), *Proc. Natl. Acad. Sci.* (*USA*) 98(22):12527-31; U.S. Prov. Appln. Ser. No. 60/345,324, filed Oct. 22, 2001), and CatSper3 (U.S. Prov. Appln. 60/401,863, filed of even date herewith). Significantly, inhibition of the activity of CatSper1 has been shown to cause a substantial decrease in the motility of sperm cells, particularly the most vigorous sperm tail beating required for penetration of the zona pellucida (ZP) and subsequent fertilization, and CatSper1 knock-out mice have been shown to be infertile. Like CatSper1 and the other members of the CatSper family of proteins, the CatSper4 protein includes six transmembrane domains and a pore region, its expression is strictly localized to testis (e.g., spermatocytes and the principal piece of sperm), and its function appears related to cyclic nucleotide-mediated calcium entry and motility. Data indicate that the CatSper proteins may heteromultimerize to function in vivo.

The CatSper4 gene encodes six transmembrane domains and a pore region. The gene product is exclusively expressed in the testis and not in other tissues such as the heart, brain, spleen, lung, liver, skeletal muscle, or kidney. In sperm, the channel is localized primarily to the tail's principal piece, not the head or midpiece.

Agonists and antagonists of the activity of the CatSper4 protein can modulate sperm motility and, therefore, can be used to treat infertility or as male and female contraceptives.

The patent, scientific and medical publications referred to herein establish knowledge that was available to those of ordinary skill in the art at the time the invention was made. The entire disclosures of the issued U.S. patents, published and pending patent applications, and other references cited herein are hereby incorporated by reference. In particular, the entire disclosures of U.S. Prov. Appln. Ser. No. 60/288,402, filed May 3, 2001, U.S. Prov. Appln. Ser. No. 60/327,167, filed Oct. 4, 2001, U.S. Prov. Appln. Ser. No. 60/345,324, filed Oct. 22, 2001, and PCT Intl. Appln. No. PCT/US02/13487, filed May 3, 2002, are incorporated herein by reference.

DEFINITIONS

All technical and scientific terms used herein, unless otherwise defined below, are intended to have the same meaning as commonly understood by one of ordinary skill in the art; references to techniques employed herein are intended to refer to the techniques as commonly understood in the art, including variations on those techniques or substitutions of equivalent techniques which would be apparent to one of skill in the art. In order to more clearly and concisely describe the subject matter which is the invention, the following definitions are provided for certain terms which are used in the specification.

As used herein, the term "CatSper4 protein" means a sperm-specific cation channel such as the human CatSper4 protein disclosed in SEQ ID NO: 2, human allelic variants of the disclosed CatSper4 protein, mammalian homologs of these human CatSper4 proteins, and functional equivalents thereof. The term CatSper4 protein refers to naturally occurring proteins as isolated from sperm, recombinantly produced proteins from cells transformed with CatSper4 genes, and fusion proteins in which CatSper4 sequences are fused to N-terminal or C-terminal polypeptides. The term "fragment" refers to fragments of the CatSper4 proteins, such as structural domains and epitopes. A fragment of a CatSper4 protein comprises at least six amino acid residues.

As used herein, the term "CatSper4 gene" means a gene encoding a CatSper4 protein, including the human CatSper4 protein disclosed in SEQ ID NO: 2, human allelic variants of the disclosed CatSper4 protein, mammalian homologs of these human CatSper4 proteins, and functional equivalents thereof. The term CatSper4 gene refers to both naturally occurring genes as isolated from genomic DNA, and recombinantly produced genes in which the CatSper4 coding regions are operably joined to either endogenous or exogenous regulatory elements, with or without intron sequences, and with or without 5' or 3'-flanking sequences which can encode heterologous (i.e., non-CatSper4) sequences to form a CatSper4 fusion protein. A CatSper4 gene will include, at a minimum, a coding region encoding the protein operably joined to regulatory elements (e.g., promoters, enhancer) which allow transcription of the coding region to mRNA which can be translated into a CatSper4 protein.

As used herein "CatSper4" activity means any normal biological activity of a wild-type CatSper4 protein when expressed in a cell or cell type in which CatSper4 is normally expressed and under conditions under which CatSper4 is normally expressed. Such activity can include induction of an ion current; mediation of cAMP-induced $Ca^{2+}$ influx; restoration of sperm motility when expressed in CatSper4−/− sperm; and/or restoration of the ability to penetrate eggs when expressed in CatSper4−/− sperm. CatSper4 activity can be measured in sperm cells or spermatocytes, or in other cells in which any necessary accessory factors are present.

As used herein with respect to nucleic acid and amino acid sequences, the term "identity" means a measure of the degree of similarity of two sequences based upon an alignment of the sequences which maximizes identity and which is a function of the number of identical nucleotides or residues, the number of total nucleotides or residues, and the presence and length of gaps in the sequence alignment. A variety of algorithms and computer programs are available for determining sequence identity using standard parameters. For example, Gapped BLAST or PSI-BLAST (Altschul et al. (1997), Nucleic Acids Res. 25:33 89-3402), BLAST (Altschul et al. (1990) *J. Mol. Biol.* 215:403-410), and Smith-Waterman (Smith et al. (1981), *J. Mol. Biol.* 147:195-197). As used herein, percent identity is based upon the default values for the BLAST algorithms.

As used herein, the term "homolog" means a protein which is evolutionarily-related to and shares substantial, conserved structural and functional similarity with a reference protein, but which is present in a different species (e.g., human, rat, and insect CatSper4 proteins are homologs of each other).

As used herein, the term "mutation" refers to a change in a nucleic acid sequence, whether or not expressed as a change in a corresponding encoded protein sequence, relative to some reference sequence. The reference sequence can be a "wild-type" sequence (i.e., one or more high frequency sequences in a population corresponding to a "normal" phenotype), or any other sequence. As used herein, the term mutation is intended to be synonymous with the term polymorphism, and therefore the differences between any two non-identical sequences can be regarded as mutations. The term mutation is intended to encompass insertions, deletions and/or substitutions of one or more nucleotides relative to a reference sequence.

As used herein, the terms "exogenous" or "heterologous" mean, with respect to two or more genetic sequences, that the genetic sequences do not occur in the same physical relation to each other in nature and/or do not naturally occur within the same genome. For example, a genetic construct can include a coding region which is operably joined to one or more regulatory elements, and these sequences are considered heterologous to each other if they are not operably joined in nature and/or they are not found in the same genome in nature. Similarly, a genetic construct which is introduced into a cell is considered heterologous to that cell to the extent that it contains genetic sequences not found in that cell. In addition, a synthetically-produced genetic sequence based upon a naturally occurring sequence, will be heterologous to the naturally-occurring sequence to the extent codons have been altered and the synthetic sequence does not exist in nature. Allelic variants of a sequence in a species are not considered heterologous to each other.

As used herein, the term "operably joined" refers to a covalent and functional linkage of genetic regulatory elements and a genetic coding region which can cause the coding region to be transcribed into mRNA by an RNA polymerase which can bind to one or more of the regulatory elements. Thus, a regulatory region, including regulatory elements, is operably joined to a coding region when RNA polymerase is capable under permissive conditions of binding to a promoter within the regulatory region and causing transcription of the coding region into mRNA. In this context, permissive conditions would include standard intracellular conditions for constitutive promoters, standard conditions and the absence of a repressor or the presence of an inducer for repressible/inducible promoters, and appropriate in vitro conditions, as known in the art, for in vitro transcription systems.

As used herein, the term "expression" refers to the process by which a coding sequence of a gene is transcribed into a primary mRNA transcript, the primary mRNA transcript is processed into a mature mRNA, and the mature mRNA is translated into a protein. Expression can optionally include post-translation modifications of the resulting polypeptide.

As used herein, the phrase "genetic construct encoding a CatSper4 protein" means a recombinant DNA, RNA, or nucleic acid analog molecule which includes a genetic sequence encoding, or which is complementary to a genetic sequence encoding, the amino acid sequence of the CatSper4 protein, and which is capable of being expressed in a cell which has been transformed with the construct. The construct can express the CatSper4 protein transiently, or can stably integrate into the genome of the cell and express the protein conditionally or constitutively.

As used herein, the term "vector" means any genetic construct, such as a plasmid, phage, transposon, cosmid, chromosome, virus, virion, etc., which is capable transferring gene sequences between cells. Vectors can be capable of one or more of replication, expression, and insertion or integration, but need not possess each of these capabilities. Thus, the term includes cloning, expression, homologous recombination, and knock-out vectors.

As used herein, with respect to genetic engineering, the term "transform" means to introduce into a cell or an organism an exogenous nucleic acid or nucleic acid analog which replicates within that cell or organism, that encodes a polypeptide sequence which is expressed in that cell or organism, and/or that is integrated into the genome of that cell or organism so as to affect the expression of a genetic locus. The term "transform" is used to embrace all of the various methods of introducing such nucleic acids or nucleic acid analogs, including, but not limited to the methods referred to in the art as transformation, transfection, transduction, electroporation, ballistic injection, and the like.

As used herein, a "nucleic acid analog" means a molecule having sufficient structural and functional similarity to a nucleic acid to direct sequence-specific forward or reverse transcription of complementary nucleic acids, or to direct sequence-specific translation of an encoded polypeptide within a living cell.

As used herein, the term "reporter gene" means any genetic sequence which, when expressed, has a biochemical or phenotypic effect which is detectable. Reporter genes are also known in the art as "marker" genes.

As used herein, the term "antibody" is intended to embrace naturally produced antibodies, recombinantly produced antibodies, and antibody fragments such as Fab fragments, F(ab')$_2$ fragments, Fv fragments, and single-chain Fv fragment (scFv).

As used herein, the term "effective amount" of an agonist or antagonist, or an enhancer or repressor, means the total amount of the active component(s) of a composition that is sufficient to cause a statistically significant change on a detectable biochemical or phenotypic characteristic. When applied to an individual active ingredient, administered alone, the term refers to that ingredient alone. When applied to a combination, the term refers to combined amounts of the active ingredients that result in the effect, whether administered in combination, serially or simultaneously.

As used herein, the term "substantially pure" means a preparation which contains at least 60% (by dry weight) of the protein of interest, exclusive of the weight of other intentionally included compounds. Preferably the preparation is at least 75%, more preferably at least 90%, and most preferably at least 99%, by dry weight of the protein of interest, exclusive of the weight of other intentionally included compounds. Purity can be measured by any appropriate method, e.g., column chromatography, gel electrophoresis, amino acid compositional analysis or HPLC analysis. If a preparation intentionally includes two or more different proteins of the invention, a "substantially pure" preparation means a preparation in which the total dry weight of the protein of the invention is at least 60% of the total dry weight, exclusive of the weight of other intentionally included compounds. Preferably, for such preparations containing two or more proteins of the invention, the total weight of the proteins of the invention should be at least 75%, more preferably at least 90%, and most preferably at least 99%, of the total dry weight of the preparation, exclusive of the weight of other intentionally included compounds. Thus, if the proteins of the invention are mixed with one or more other compounds (e.g., diluents, detergents, excipients, salts, sugars, lipids) for purposes of administration, stability, storage, and the like, the weight of such other compounds is ignored in the calculation of the purity of the preparation.

As used herein, the term "contacted" as in the phrase "A is contacted with B," means that A and B are brought into sufficient physical proximity to interact at the molecular level, as by mixing A and B together in a solution, or pouring a solution of A over B on substrate. As used herein, the phrase "A is contacted with B" is intended to be equivalent to "B is contacted with A" and is not intended to imply that either element is fixed relative to the other, or that either element is moved relative to the other.

As used herein, the terms "modulate" or "affect" mean to either increase or decrease. As used herein, the terms "increase" and "decrease" mean, respectively, statistically significantly increase (i.e., $p<0.1$) and statistically significantly decrease (i.e., $p<0.1$).

General Considerations.

The present invention depends, in part, upon the identification, isolation and characterization of a cation channel protein which is expressed in sperm cells, but not in other tissues tested, and which plays a significant role in the motility of sperm and their ability to fertilize ova. The protein has been designated CatSper4 to indicate that it is the fourth Cation channel which is Sperm-specific to be identified.

The CatSper4 gene encodes six transmembrane domains and a pore region. The gene product is exclusively expressed in the testis and not in other tissues such as the heart, brain, spleen, lung, liver, skeletal muscle, or kidney. In sperm, the channel is localized primarily to the tail's principal piece, not the head or midpiece.

Agonists and antagonists of the activity of the CatSper4 protein can modulate sperm motility and, therefore, can be used to treat infertility or as male and female contraceptives. In particular, CatSper4 represents an excellent target for non-hormonal contraceptives for both males and females, including humans and other mammals. Identification of the CatSper4 gene and protein also presents new targets for the diagnosis and treatment of infertility, and thus provides for new assays for the identification of compounds that can modulate fertility.

CatSper4 Nucleic Acids.

In one aspect, the present invention provides nucleic acid molecules, or nucleic acid analogs, encoding the CatSper4 proteins, or useful fragments thereof. The full length cDNA of the human CatSper4 gene is disclosed as SEQ ID NO: 1. The full-length cDNA sequence of a murine homolog is disclosed as SEQ ID NO: 3. The 5' regulatory region of a human allele, including 6358 bases extending 5' from the translational start codon, is disclosed as SEQ ID NO: 5. The 5' untranslated region of this human allele is disclosed as SEQ ID NO: 6. The 3' untranslated region of this human allele, including 72 bases extending 3' from the translational termination codon, is disclosed as SEQ ID NO: 7.

Nucleic acid molecules of the invention can be DNA or RNA molecules, or hybrid DNA-RNA molecules. The nucleic acid analogs of the invention can be any of those known in the art, such as peptide nucleic acids, analogs including modified bases (e.g., 2'-halogeno-2'-dexynucleosides) and/or analogs including modified internucleoside linkages (e.g., phosphorothioate linkages), which are useful in applications such as in vitro translation or antisense technologies. In the remainder of this disclosure and the appended claims, whenever the term "nucleic acids" is used, the term is intended to embrace nucleic acid analogs when such analogs would be useful or suitable in the context of the usage. The nucleic acids can be sense molecules corresponding to all or a portion of a CatSper4 gene sequence, or can be antisense molecules which are complementary to all or a portion of a CatSper4 gene sequence. The nucleic acids can be derived from or correspond to genomic DNA or cDNA, or can be synthetic molecules based upon a CatSper4 protein sequence and the genetic code (e.g., synthetic nucleic acids which reflect the codon usage preferences in the host cells used in an expression systems).

In some embodiments, the CatSper4 nucleic acids comprise the entire coding region of a CatSper4 gene (e.g., SEQ ID NO: 1 or SEQ ID NO: 3). Such nucleic acids can be used to produce genetic constructs for transformation of cells, or for in vitro transcription and translation systems. Such nucleic acids can also be used as probes in hybridization assays to detect CatSper4 sequences in samples of other nucleic acids.

In other embodiments, subsets of the CatSper4 nucleic acid sequences are provided for use as primers for nucleic acid amplification reactions, as probes in hybridization assays to detect CatSper4 sequences in samples of other nucleic acids, or as probes to distinguish normal or wild-type sequence from abnormal or mutant sequences. In these embodiments, the nucleic acids of the invention comprise at 10, preferably at least 12, more preferably at least 14 and most preferably at least 16 consecutive nucleotides selected from a CatSper4 sequence such as SEQ ID NO: 1. Depending upon the nature of the application, it may be preferable to choose CatSper4 sequences which will have unique targets, or which are expected to have unique targets, within a sample being probed or amplified. Thus, for example, sequences which are longer and sequences which do not include frequently repeated elements (for example, polyadenylation signals) are more likely to be uniquely represented within any given sample. For purposes of choosing primers for amplification reactions, sequences of at least 15, and preferably 18-25 nucleotides are preferred.

In certain preferred embodiments, nucleic acids are provided which encode structural domains of a CatSper4 protein, or which encode fragments of the protein which can serve as epitopes for the generation of antibodies. Thus, for example, preferred nucleic acids include those encoding the transmembrane domains of the CatSper4 proteins (i.e., approximately residues 46-75, 86-98, 108-137, 155-202, 209-233 and 242-272 of SEQ ID NO: 2, approximately residues 48-73, 81-111, 113-134, 156-204, 208-233 and 245-273 of SEQ ID NO: 4, and allelic variants and homologs thereof), encoding the extracellular loops between transmembrane domains (i.e., approximately residues 76-85, 138-154 and 234-242 of SEQ ID NO: 2, approximately residues 74-80, 135-155 and 234-244 of SEQ ID NO: 4, and allelic variants and homologs thereof), or encoding the pore region (i.e., approximately residues 222-231 of SEQ ID NO: 2, approximately residues 222-231 of SEQ ID NO: 4, and allelic variants and homologs thereof). Other preferred nucleic acids include those encoding epitopes of the CatSper4 proteins having high predicted antigenicity, as identified by standard sequence analysis techniques described below. Thus, for example, preferred nucleic acids include those encoding sequences within a high predicted antigenicity epitope of SEQ ID NO: 2, or within a high predicted antigenicity epitope of SEQ ID NO: 4, and allelic and mammalian homologs thereof.

In certain embodiments, nucleic acids are provided which encode polypeptides have at least 80%, and preferably at least 85%, 90% or 95% amino acid sequence identity with at least a structural domain of a CatSper4 protein. Thus, in some embodiments, a nucleic acid is provided which encodes a polypeptide having at least 80%, 85%, 90% or 95% amino acid sequence identity with a transmembrane domain of a CatSper4 proteins (e.g., approximately residues 46-75, 86-98, 108-137, 155-202, 209-233 and 242-272 of SEQ ID NO: 2, approximately residues 48-73, 81-111, 113-134, 156-204, 208-233 and 245-273 of SEQ ID NO: 4, and allelic variants and homologs thereof), an extracellular loop between transmembrane domains (e.g., approximately residues 76-85, 138-154 and 234-242 of SEQ ID NO: 2, approximately residues 74-80, 135-155 and 234-244 of SEQ ID NO: 4, and allelic variants and homologs thereof), or a pore region (e.g., approximately residues 222-231 of SEQ ID NO: 2, approximately residues 222-231 of SEQ ID NO: 4, and allelic variants and homologs thereof). In some preferred embodiments, nucleic acids are provided encoding a polypeptide having at least 80%, 85%, 90% or 95% amino acid sequence identity with a CatSper4 protein and having CatSper4 activity. The ability of a protein to exhibit CatSper4 activity can be measured by its ability to complement a CatSper4−/− mutant (e.g., a CatSper4 knock-out mutant) and restore a normal or CatSper4+/+ phenotype (e.g., to restore sperm motility) in a cell otherwise capable of expressing CatSper4 activity (e.g., a sperm cell from the CatSper4−/− mutant).

In other embodiments, isolated nucleic acids are provided which include a nucleotide sequence that hybridizes to at least a portion of a CatSper4 coding sequence (e.g., SEQ ID NO: 1 or SEQ ID NO: 3) under stringent hybridization conditions. Such conditions include hybridizations employing a wash step of 1.0×SSC at 65° C., and equivalents thereof. More stringent conditions can include wash steps of 0.5×SSC, 0.2× SSC, or even 0.1×SSC. Other equivalently stringent conditions are well known in the art. See, e.g., Ausubel et al., eds.

(1989), Current Protocols in Molecular Biology, Vol. I, John Wiley & Sons, Inc., New York. In preferred embodiments, the nucleic acid encodes a polypeptide having CatSper4 activity.

In another aspect, the invention provides nucleic acids, either isolated or existing within cells, in which a nucleotide sequence encoding a polypeptide having CatSper4 activity is operably joined to a heterologous regulatory region such that the CatSper4 sequence is expressed. Thus, in certain embodiments, a heterologous regulatory region can be inserted into a chromosome such that it is operably joined to an endogenous CatSper4 sequence. In some embodiments, the polypeptide has at least 80%, 85%, 90% or 95% amino acid sequence identity with an amino acid sequence of SEQ ID NO: 2 or 4. In other embodiments, the nucleic acid encoding the polypeptide hybridizes to at least a portion of a nucleic acid of SEQ ID NO: 1 or SEQ ID NO: 3 under conditions including a wash step of 1.0×SSC at 65° C., 0.5×SSC, 0.2×SSC, or 0.1×SSC.

In certain embodiments, the nucleic acids of the invention encode polypeptides including a CatSper4 sequence of at least 50 amino acid residues in length, and preferably at least 100, 200 or 300 amino acid residues in length. These polypeptides can include a CatSper4 sequence which includes at least one transmembrane domain, at least one extracellular loop domain, at least a pore region, or combinations thereof. In some preferred embodiments, the polypeptide has CatSper4 activity. Such activity can include induction of ion current; mediation of cAMP-induced $Ca^{2+}$ influx; restoration of sperm motility when expressed in CatSper4−/− sperm; and/or restoration of the ability to penetrate eggs when expressed in CatSper4−/− sperm.

In another aspect, the invention provides kits for detecting at least a portion of a CatSper4 nucleic acid (i.e., CatSper4 genomic DNA, mRNA, cDNA or amplification products thereof). The kits include an isolated nucleic acid of the invention as a probe and means for detecting the probe. The means for detecting the probe can be a detectable label bound to the probe or a secondary nucleic acid probe for detecting the first probe (e.g., labeled secondary nucleic acid which specifically hybridizes to the isolated nucleic acid).

Genetic Constructs.

In another aspect, the present invention provides genetic constructs comprising sequences selected from CatSper4 genes. In certain embodiments, the CatSper4 gene sequences are selected from the coding region of the CatSper4 gene, and in other embodiments, the CatSper4 gene sequences can be chosen from the CatSper4 regulatory regions extending approximately 500-1,500 bases, or approximately 600-1,000 bases, 5' of the start codon, and approximately 250-1,000 bases, or approximately 500-750 bases, 3' of the termination codon.

In one series of embodiments, CatSper4 coding sequences (e.g., the entire coding region, sequences encoding structural domains, sequences encoding potential epitopes, or sequences encoding useful primers or probes) are operably joined to an endogenous or exogenous regulatory region to form an expression construct. Useful regulatory regions for these purposes include the endogenous CatSper4 regulatory region, constitutive promoter sequences (e.g., CMV, SV40, EF2), inducible promoter sequences (e.g., lacZ, tet). Many useful vector systems are now widely available. For example, useful bacterial vectors include, but are not limited to, pQE70, pQE60, pQE-9 (Qiagen, Valencia, Calif.), pBluescript II (Stratagene, La Jolla, Calif.), and pTRC99a, pKK223-3, pDR540 and pRIT2T (Pharmacia, Piscataway, N.J.), pTrc (Amann et al. (1988), *Gene* 69:301-315) and pET 11d (Studier et al. (1990), *Methods in Enzymol.* 185:60-89). Examples of vectors for expression in yeast include pYepSec1 (Baldari et al. (1987), *EMBO J.* 6:229-234), pMFa (Kurjan et al. (1982), *Cell* 30:933-943), pJRY88 (Schultz et al. (1987), *Gene* 54:113-123), and pYES2 (Invitrogen Corporation, San Diego, Calif.). The CatSper4 proteins can also be expressed in insect cells (e.g., Sf 9 cells) using, for example, baculovirus expression vectors including, but not limited to, pAc vectors (Smith et al. (1983), *Mol. Cell Biol.* 3:2156-2165) and pVL vectors (Lucklow et al. (1989), *Virology* 170:31-39). Examples of mammalian expression vectors include, but are not limited to, pCDM8 (Seed (1987), *Nature* 329:840) and pMT2PC (Kaufman et al. (1987), *EMBO J.* 6:187-195). Other useful eukaryotic vectors include, but are not limited to, pXT1, pSG5 (Stratagene, La Jolla, Calif.), and pSVK3, pBPV, pMSG, and PSVLSV40 (Pharmacia, Piscataway, N.J.). Thus, one of ordinary skill in the art can choose a vector system appropriate to the host cell to be transformed.

In other embodiments, the vectors comprise defective or partial CatSper4 sequences in a "knock-out" vector. Such vectors are well-known in the art and can be used to produce a transgenic organism in which an endogenous gene is "knocked-out" by recombination with a partially homologous exogenous sequence which introduces a mutation within the endogenous sequence. Typically, the vector is directed at an endogenous target sequences which can be all or part of a gene of interest. The vector includes 5' and 3' flanking sequences which are homologous to the 5' and 3' ends of the target. Between the 5' and 3' flanking sequences is the sequence including the mutation. The mutation can be a termination mutation, frame-shift mutation, large deletion, or even the introduction of a new coding sequence which serves both to disrupt the endogenous gene and to act as a marker for successful homologous recombination. Knock-out vectors are further discussed below.

In other embodiments, the CatSper4 coding sequences can be joined to regulatory regions and heterologous coding sequences to form a genetic construct or fusion vector which encodes a fusion protein. Fusion vectors and fusion proteins can be useful to increase the expression of the CatSper4 protein, to increase the solubility of the CatSper4 protein, and aid in the purification of the CatSper4 protein (e.g., by acting as a ligand for affinity purification). A proteolytic cleavage site can be introduced at the junction of the CatSper4 and non-CatSper4 protein sequences so that the CatSper4 protein can easily be separated from the fusion moiety. Typical fusion expression vectors include pGEX (Smith et al. (1988), *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

In another series of embodiments, vectors or genetic constructs are produced in which the coding region from a reporter gene is operably joined to the regulatory region of a CatSper4 gene (e.g., SEQ ID NO: 5 and, optionally, SEQ ID NO: 6 at the 5' end and, optionally, SEQ ID NO: 7 at the 3' end). Such genetic constructs are useful in assays to identify or characterize compounds that enhance or repress CatSper4 gene expression by enhancing or repressing transcription of the CatSper4 gene. A wide variety of suitable reporter genes are known to those of skill in the art, and are commercially available. Examples include, but are not limited to, the lacZ and luciferase genes.

Useful CatSper4 regulatory elements include sequences having at least 80% nucleotide identity to at least 100 consecutive nucleotides selected from SEQ ID NO: 5, preferably at least 200 consecutive nucleotides, and more preferably at least 300-500 consecutive nucleotides. Useful regulatory elements will retain the ability to promote transcription of a coding sequence operably joined to the element in a mammalian cell in which a CatSper4 gene is expressed. In particular, useful regulatory elements will retain the ability to promote transcription in cells in which the CatSper4 gene from which the element was derived is expressed, or in which a homolog of that CatSper4 gene is expressed.

Transformed Cell Lines.

In another aspect, the present invention provides cell lines transformed with the nucleic acid molecules of the invention. Such cell lines can simply propagate these nucleic acids (e.g., when transformed with cloning vectors) or can express the polypeptides encoded by these nucleic acids (e.g., when transformed with expression vectors). Such transformed cell lines can be used to produce the CatSper4 proteins and CatSper4 fragments of the invention, or can be used in assays to screen for compounds that enhance, repress, agonize, or antagonize CatSper4 expression or activity.

The transformed cells can be produced by introducing into a cell an exogenous nucleic acid or nucleic acid analog which replicates within that cell, that encodes a polypeptide sequence which is expressed in that cell, and/or that is integrated into the genome of that cell so as to affect the expression of a genetic locus. The transformation can be achieved by any of the standard methods referred to in the art as transformation, transfection, transduction, electroporation, ballistic injection, and the like. The method of transformation is chosen to be suitable to the type of cells being transformed and the nature of the genetic construct being introduced into the cells.

Preferred cell lines for transformation include bacterial cells (e.g., *Escherichia coli*), yeast cells (e.g., *Saccharomyces cerevisiae*), insect cells (e.g., *Drosophila melanogaster* Schneider cells), nematode cells (e.g., *Caenorhabditis elegans*), amphibian cells (e.g., *Xenopus* oocytes), rodent cells (e.g., *Mus musculus* (e.g., murine 3T3 fibroblasts), *Rattus rattus*, Chinese Hamster Ovary cells (e.g., CHO-K1)), and human cells (e.g., human skin fibroblasts, human embryonic kidney cells (e.g., HEK-293 cells), COS cells, spermatogonial cells). Transformed mammalian cells useful in the invention include somatic cells, fetal cells, embryonic stem cells, zygotes, gametes, germ line cells and transgenic animal cells.

Appropriate cells can be transformed with any of the above-described genetic constructs in order to produce CatSper4 proteins, including fragments of CatSper4 proteins, fusion proteins of CatSper4 proteins, or marker proteins under the control of a CatSper4 regulatory region.

The cells can be transformed according to any method known in the art appropriate to the cell type being transformed. Appropriate methods can include those described generally in, e.g., Sambrook et al. (1989), *Molecular Cloning: A Laboratory Manual*, Cold Spring Harbor Laboratories, New York; and Davis et al. (1986), *Basic Methods in Molecular Biology*, Elsevier. Particular methods include calcium phosphate co-precipitation (Graham et al. (1973), *Virol.* 52:456-467), direct micro-injection into cultured cells (Capecchi (1980), *Cell* 22:479-488), electroporation (Shigekawa et al. (1988), *BioTechniques* 6:742-751), liposome-mediated gene transfer (Mannino et al. (1988), *BioTechniques* 6:682-690), lipid-mediated transduction (Felgner et al. (1987), *Proc. Natl. Acad. Sci. USA* 84:7413-7417), and nucleic acid delivery using high-velocity microprojectiles (Klein et al. (1987), *Nature* 327:70-73).

Transgenic Animals.

The present invention also provides for the production of transgenic non-human animal models in which wild type, allelic variant, chimeric, or antisense CatSper4 sequences are expressed, or in which CatSper4 sequences have been inactivated or deleted (e.g., "knock-out" constructs) or replaced with reporter or marker genes (e.g., "knock-in reporter" constructs). The CatSper4 sequences can be conspecific to the transgenic animal (e.g., murine sequences in a transgenic mouse) or transpecific to the transgenic animal (e.g. human sequence in a transgenic mouse). In such a transgenic animal, the transgenic sequences can be expressed inducibly, constitutively or ectopically. Expression can be tissue-specific or organism-wide. Engineered expression of CatSper4 sequences in tissues and cells not normally containing CatSper4 gene products can cause novel alterations of cation flux and lead to novel cell or tissue phenotypes. Ectopic or altered levels of expression of CatSper4 sequences can alter cell, tissue and/or developmental phenotypes. Transgenic animals are useful as models of disorders arising from defects in CatSper4 activity.

Transgenic animals are also useful for screening compounds for their effects on CatSper4 activity. Transgenic animals transformed with reporter constructs can be used to measure the transcriptional effects of small molecules or drugs or physical perturbations on the expression of CatSper4 genes and proteins in vivo. The transgenic animals of the invention, can be used to screen such compounds for therapeutic utility.

Animal species suitable for use in the animal models of the present invention include, but are not limited to, rats, mice, hamsters, guinea pigs, rabbits, dogs, cats, goats, sheep, pigs, and non-human primates (e.g., Rhesus monkeys, chimpanzees). For initial studies, transgenic rodents (e.g., mice) are preferred due to their relative ease of maintenance and shorter life spans. Transgenic non-human primates may be preferred for longer term studies due to their greater similarity to humans.

Using the nucleic acids disclosed and otherwise enabled herein, there are several available approaches for the creation of a transgenic animal. Thus, the enabled animal models include: (1) animals in which sequences encoding at least a functional fragment of a CatSper4 gene has been recombinantly introduced into the genome of the animal as an additional gene, under the regulation of either an exogenous or an endogenous promoter element, and as either a minigene (i.e., a genetic construct of the CatSper4 gene based on cDNA with introns removed) or a large genomic fragment; (2) animals in which sequences encoding at least a functional fragment of a CatSper4 gene have been recombinantly substituted for one or both copies of the animal's endogenous CatSper4 gene by homologous recombination or gene targeting; (3) animals in which one or both copies of one of the animal's homologous CatSper4 genes have been recombinantly "humanized" by the partial substitution of sequences encoding the human homolog by homologous recombination or gene targeting; (4) animals in which sequences encoding a reporter gene have replaced the endogenous CatSper4 gene by homologous recombination; (5) and "knock-out" animals in which one or both copies of the animal's CatSper4 sequences have been partially or completely inactivated by the insertion, deletion or substitution of one or more nucleotides by homologous recombination. These and other transgenic animals of the invention are useful as models of infertility or other disorders arising from defects in the CatSper4 gene and/or protein. These animals are also useful for screening compounds for their effects on the CatSper4 gene and/or protein.

To produce an animal model (e.g., a transgenic mouse), a wild type or allelic variant CatSper4 sequence or a wild type or allelic variant of a recombinant nucleic acid encoding at least a functional fragment of a CatSper4 protein is preferably inserted into a germ line or stem cell using standard techniques of oocyte or embryonic stem cell microinjection, or other form of transformation of such cells. Alternatively, other cells from an adult organism can be employed. Animals produced by these or similar processes are referred to as transgenic. Similarly, if it is desired to inactivate or replace an endogenous CatSper4 sequence, homologous recombination using oocytes, embryonic stem or other cells can be employed. Animals produced by these or similar processes are referred to as "knock-out" (inactivation) or "knock-in" (replacement) models.

For oocyte injection, one or more copies of the recombinant DNA constructs of the present invention can be inserted into the pronucleus of a just-fertilized oocyte. This oocyte is then reimplanted into a pseudo-pregnant foster mother. The live born animals are screened for integrants using standard DNA/mRNA analysis (e.g., from the tail veins of offspring mice) for the presence of the inserted recombinant transgene sequences. The transgene can be either a complete genomic sequence introduced into a host as part of a yeast artificial chromosome (YAC), bacterial artificial chromosome (BAC), or other chromosome DNA fragment; as a cDNA with either the endogenous promoter or a heterologous promoter; or as a minigene containing all of the coding regions and other elements found to be necessary for optimum expression.

To create a transgene, the target sequence of interest (e.g., a wild type or allelic variant of a CatSper4 sequence) is typically ligated into a cloning site located downstream of a promoter element which will regulate the expression of RNA from the sequence. Downstream of the coding sequence, there is typically a polyadenylation sequence. An alternative approach to creating a transgene is to use an exogenous promoter and regulatory sequences to drive expression of the transgene. Finally, it is possible to create transgenes using large genomic DNA fragments such as YACs which contain the entire desired gene as well as its appropriate regulatory sequences.

Animal models can be created by targeting endogenous CatSper4 sequences for homologous recombination. These targeting events can have the effect of removing endogenous sequence (knock-out) or altering the endogenous sequence to create an amino acid change associated with human disease or an otherwise abnormal sequence (e.g., a sequence which is more like the human sequence than the original animal sequence) (knock-in animal models). A large number of vectors are available to accomplish this and appropriate sources of genomic DNA for mouse and other animal genomes to be targeted are commercially available (e.g., GenomeSystems Inc., St. Louis, Mo.).

The typical feature of these targeting vector constructs is that 2 to 4 kb of genomic DNA is ligated 5' to a selectable marker (e.g., a bacterial neomycin resistance gene under its own promoter element termed a "neomycin cassette"). A second DNA fragment from the gene of interest is then ligated downstream of the neomycin cassette but upstream of a second selectable marker (e.g., thymidine kinase). The DNA fragments are chosen such that mutant sequences can be introduced into the germ line of the targeted animal by homologous replacement of the endogenous sequences by either one of the sequences included in the vector. Alternatively, the sequences can be chosen to cause deletion of sequences that would normally reside between the left and right arms of the vector surrounding the neomycin cassette. The former is known as a knock-in, the latter is known as a knock-out.

Retroviral infection of early embryos can also be done to insert the recombinant DNA constructs of the invention. In this method, the transgene (e.g., a wild type or allelic variant of a CatSper4 sequence) is inserted into a retroviral vector which is used to directly infect embryos (e.g., mouse or non-human primate embryos) during the early stages of development to generate partially transgenic animals, some of which bear the transgenes in germ line cells.

Alternatively, homologous recombination using a population of stem cells allows for the screening of the population for successful transformants. Once identified, these can be injected into blastocysts, and a proportion of the resulting animals will show germ line transmission of the transgene.

Techniques of generating transgenic animals, as well as techniques for homologous recombination or gene targeting, are now widely accepted and practiced. A laboratory manual on the manipulation of the mouse embryo, for example, is available which details standard laboratory techniques for the production of transgenic mice (Hogan, et al. (1986), Manipulating the Mouse Embryo, Cold Spring Harbor Laboratory Press, Cold Spring Harbor, N.Y.).

CatSper4 Proteins and Polypeptides.

In another aspect, the present invention provides substantially pure preparations of CatSper4 proteins. The proteins can be isolated from sperm cells, using standard techniques such as immunoaffinity purification with the antibodies of the invention (see below), but are preferably isolated from the transformed cells of the invention, in which they can be expressed at higher levels and, optionally, as fusion proteins which are more easily isolated and/or purified.

In some embodiments, the CatSper4 proteins comprise the entire translated sequence of the CatSper4 coding region. Examples of such full-length CatSper4 proteins include the human CatSper4 protein disclosed as SEQ ID NO: 2 and the murine homolog disclosed as SEQ ID NO: 4, as well as other CatSper4 proteins, including allelic and mammalian homologs of these human CatSper4 proteins, and functional equivalents thereof.

In other embodiments, the CatSper4 proteins are CatSper4 fragments. Such fragments include the structural domains of the CatSper4 proteins, including the transmembrane, loop and pore-forming regions of the proteins. Preferred structural domains include the transmembrane domains of the human CatSper4 protein (i.e., approximately residues 46-75, 86-98, 108-137, 155-202, 209-233 and 242-272 of SEQ ID NO: 2, approximately residues 48-73, 81-111, 113-134, 156-204, 208-233 and 245-273 of SEQ ID NO: 4, the extracellular loops between transmembrane domains (i.e., approximately residues 76-85, 138-154 and 234-242 of SEQ ID NO: 2, approximately residues 74-80, 135-155 and 234-244 of SEQ ID NO: 4), and the pore region (i.e., approximately residues 222-231 of SEQ ID NO: 2, approximately residues 222-231 of SEQ ID NO: 4), as well as allelic variants and homologs thereof. Other CatSper4 fragments include potentially useful epitopes of the CatSper4 proteins, as identified by standard sequence analysis techniques described below. Thus, for example, preferred CatSper4 fragments include human CatSper4 sequences within a high predicted antigenicity epitope of SEQ ID NO: 2, or within a high predicted antigenicity epitope of SEQ ID NO: 4, and allelic and mammalian homologs thereof.

In certain embodiments, polypeptides are provided having at least 80%, and preferably at least 85%, 90% or 95% amino acid sequence identity with at least a structural domain of a CatSper4 protein. Thus, in some embodiments, a polypeptide is provided having at least 80%, 85%, 90% or 95% amino acid sequence identity with a transmembrane domain of a CatSper4 proteins (e.g., approximately residues 46-75, 86-98, 108-137, 155-202, 209-233 and 242-272 of SEQ ID NO: 2, approximately residues 48-73, 81-111, 113-134, 156-

204, 208-233 and 245-273 of SEQ ID NO: 4, and allelic variants and homologs thereof), an extracellular loop between transmembrane domains (e.g., approximately residues 76-85, 138-154 and 234-242 of SEQ ID NO: 2, approximately residues 74-80, 135-155 and 234-244 of SEQ ID NO: 4, and allelic variants and homologs thereof), or a pore region (e.g., approximately residues 222-231 of SEQ ID NO: 2, approximately residues 222-231 of SEQ ID NO: 4, and allelic variants and homologs thereof). In some preferred embodiments, polypeptides are provided having at least 80%, 85%, 90% or 95% amino acid sequence identity with a CatSper4 protein and having CatSper4 activity. The ability of a protein to exhibit CatSper4 activity can be measured by its ability to complement a CatSper4−/− mutant (e.g., a CatSper4 knock-out mutant) and restore a normal or CatSper4+/+ phenotype (e.g., to restore sperm motility) in a cell otherwise capable of expressing CatSper4 activity (e.g., a sperm cell from the CatSper4−/− mutant).

In certain embodiments, the polypeptides of the invention include a CatSper4 sequence of at least 50 amino acid residues in length, and preferably at least 100, 200 or 300 amino acid residues in length. These polypeptides can include a CatSper4 sequence which includes at least one transmembrane domain, at least one extracellular loop domain, at least a pore region, or combinations thereof. In some preferred embodiments, the polypeptide has CatSper4 activity. Such activity can include induction of ion current when expressed in a cell (e.g., an oocyte); mediation of cAMP-induced $Ca^{2+}$ influx; restoration of sperm motility when expressed in CatSper4−/− sperm; and/or restoration of the ability to penetrate eggs when expressed in CatSper4−/− sperm.

Antibodies Against CatSper4 Proteins and Polypeptides.

In another aspect, the present invention provides substantially pure preparations of antibodies against the CatSper4 proteins, and methods of making such antibodies. In particular, the invention provides antibodies raised against CatSper4 epitopes having high predicted antigenicity, which therefore will selectively bind to and, thereby, isolate or identify wild type and/or variant forms of the CatSper4 proteins.

The antibodies can be raised against the full-length CatSper4 proteins, against fragments of the CatSper4 proteins, or using any CatSper4 epitope which is characteristic of the proteins and which substantially distinguishes them from other proteins. In preferred embodiments, the epitope is a protein sequence of at least 6-12, preferably 10-20, more preferably 15-30 consecutive amino acid residues of a CatSper4 protein. In particular embodiments, the antibodies are raised against CatSper4 epitopes selected from sequences within a high predicted antigenicity epitope of SEQ ID NO: 2, or within a high predicted antigenicity epitope of SEQ ID NO: 4. Other preferred epitopes include allelic and mammalian homologs of these epitopes. Epitopes having a high predicted antigenicity were identified by prediction of hydrophobicity, surface probability and antigenic index using standard programs, including GCG and MacVector (Genetics Computer Group, University of Wisconsin Biotechnology Center, Madison, Wis.; Accelrys Inc., San Diego, Calif.). See also, Jameson and Wolf (1988), Comput. Appl. Biosci. 4:181-186.

CatSper4 immunogen preparations can be produced from crude extracts (e.g., microsomal fractions of cells expressing the proteins), from proteins or peptides substantially purified from cells which naturally or recombinantly express them or, for small immunogens, by chemical peptide synthesis. The CatSper4 immunogens can also be in the form of a fusion protein in which the non CatSper4 region is chosen for its adjuvant properties and/or the ability to facilitate purification.

The antibodies of the invention can be polyclonal or monoclonal, or can be antibody fragments, including Fab fragments, $F(ab')_2$ fragments, Fv fragments, and single chain Fv fragments (scFv). In addition, after identifying useful antibodies by the method of the invention, recombinant antibodies can be generated, including any of the antibody fragments listed above, as well as chimeric and/or humanized antibodies based upon non-human antibodies to the CatSper4 proteins. In light of the present disclosure of CatSper4 proteins, as well as the characterization of other CatSper4 proteins enabled herein, one of ordinary skill in the art can produce the above-described antibodies by any of a variety of standard means. For an overview of antibody techniques, see Antibody Engineering, 2nd Ed., Borrebaek, ed., Oxford University Press, Oxford (1995).

As a general matter, monoclonal anti-CatSper4 antibodies can be produced by first injecting a mouse, rabbit, goat or other suitable animal with a CatSper4 immunogen in a suitable carrier or diluent. Carrier proteins or adjuvants can be utilized, and booster injections (e.g., bi- or tri-weekly over 8-10 weeks) can be employed as necessary. After allowing for development of a humoral response, the animals are sacrificed and their spleens are removed and resuspended in an appropriate buffer (e.g., phosphate buffered saline). The spleen cells serve as a source of lymphocytes, some of which will produce antibodies of the appropriate specificity. These cells are then fused with an immortalized cell line (e.g., a myeloma), and the products of the fusion are plated into tissue culture wells in the presence of a selective agent (e.g., HAT). The wells are serially screened and replated, selecting cells making a useful antibody each time. Typically, several screening and replating procedures are carried out until the wells contain single clones which are positive for antibody production. Monoclonal antibodies produced by such clones can be purified by standard methods such as affinity chromatography using Protein A Sepharose, by ion-exchange chromatography, or by variations and combinations of these techniques.

Antibodies of the invention can be used in a variety of applications. For example, antibodies can be used in a purification process (i.e., immunoaffinity purification) for CatSper4 proteins, in assays to detect the presence or level of CatSper4 protein in sperm (e.g., in a diagnostic test for a CatSper4-related disorder), or in assays to measure the presence or level of CatSper4 expression in transformed cells (e.g., in assays for regulators of CatSper4 expression, in Western blotting to identify cells expressing CatSper4 proteins, or in immunocytochemistry or immunofluorescence techniques to establish the cellular or extracellular location of CatSper4 proteins).

The antibodies of the invention can be bound or conjugated with other compounds or materials for diagnostic and/or therapeutic uses. For example, they can be coupled to labels such as radionuclides, fluorescent compounds (e.g., rhodamine), or enzymes for imaging or therapy. The labels can be bound to the antibodies covalently or non-covalently.

In another aspect, the invention provides kits for detecting at least an epitope of a CatSper4 protein. The kits include an anti-CatSper4 antibody and a means for detecting the antibody. The means for detecting the antibody can be a detectable label bound to the antibody or secondary antibodies for detecting the anti-CatSper4 antibodies (e.g., a labeled goat anti-rabbit-Ig antibody as a secondary antibody for detecting a rabbit anti-CatSper4 antibody).

Assays for Modulators of CatSper4 Expression or Activity.

In another aspect, the present invention provides assays for modulators of CatSper4 expression or activity. The modulators can affect the transcription, translation, post-translational processing, localization, or activity of the CatSper4 gene and/or protein.

Thus, in one series of embodiments, the transformed cells of the invention are contacted with a candidate compound, and the effect of the compound on the expression or activity of CatSper4 is determined. As a general matter, the assays require contacting a candidate compound with a cell expressing a CatSper4 protein and measuring an indicator of CatSper4 activity in the cell. The indicator can be an indicator of transcription (e.g., mRNA levels), translation (e.g., protein levels), post-translational processing (e.g., specific glycosylation), localization (e.g., immunohistochemistry), or activity (e.g., sodium or other monovalent ion flux; calcium or other divalent ion flux). The indicator measurement is then compared to a reference level to determine whether the candidate compound caused an increase or decrease in the indicator. The reference level can be extrinsic (e.g., a predetermined baseline level) or intrinsic (e.g., a measurement of the same cell prior to contact with the candidate compound). If an increase or decrease is significant (based on a single reading or on multiple readings from one or more cells), the candidate compound is identified as a potential modulator of CatSper4 activity. Assays for changes in CatSper4 activity can include any of those used routinely in the art for other genes. For example, changes in the presence or levels of CatSper4 mRNA or protein can be detected to identify enhancers or repressors of CatSper4 expression. Alternatively, when using a reporter gene construct of the invention, the biochemical or phenotypic change characteristic of the reporter can be used as an indication that the candidate compound enhances or represses reporter gene expression. In other embodiments, changes in the activity of the CatSper4 protein can be detected by measuring, for example, the flux of cations mediated by the CatSper4 protein, or by measuring whole cell or channel currents. Measurements of ion fluxes can be facilitated by the use of chromophores which change color depending upon the concentration of specific ions. The effects of candidate compounds on mature sperm cells can be tested to confirm or validate results obtained in the transformed cells of the invention.

Compounds which bind to CatSper4 are candidates for modulating CatSper4 activity. Thus, in another series of embodiments, libraries of compounds can be screened to identify candidates for modulating CatSper4 activity by contacting candidate compounds with a CatSper4 protein, or at least a structural domain of a CatSper4 protein, to identify compounds that bind to CatSper4. CatSper4 structural domains which can be used in these methods include those described above (i.e., transmembrane domains, extracellular loops, pore regions), but extracellular loops and pore regions are preferred. In such methods, the CatSper4 protein or CatSper4 structural domain can be immobilized (e.g., on a column or microparticle) and a solution of the candidate compound can be contacted with the CatSper4 moiety, or the candidate compound can be immobilized (e.g., on a column or microparticle) and a solution of the CatSper4 moiety can be contacted with the candidate compound. Alternatively, in some embodiments, neither the candidate compound nor the CatSper4 moiety is immobilized but, rather, both are in solution and binding is detected by, for example, aggregation of particles bearing the binding partners. Binding can be detected by methods well known in the art (e.g., radioactive or fluorescent labeling of one component of the potential binding pair; plasmon-resonance detection of binding; turbidity changes in aggregation assays). Compounds which, under physiological conditions (e.g., within the testis or epididymis, or within the vagina, uterus or fallopian tubes), exhibit significant binding (e.g., $K_d \leq 10$ μM) to a CatSper4 protein, are potential modulators of CatSper4 activity.

Methods of Modulating Fertility.

The CatSper4 gene and protein are ideal targets for potential contraceptive drugs. The restricted localization of CatSper4 to mature sperm means that a specific blocker should not affect other tissues and thus side effects should be low or nonexistent. Finally, since the channel represents a novel structure, it may be an excellent target for new channel agonists or antagonists.

Thus, in another aspect, the present invention provides methods of decreasing fertility by decreasing the expression or activity of a CatSper4 gene or protein. Such decreases in expression or activity can be achieved by means of a small molecule which represses expression of a CatSper4 gene, by means of an antisense molecule which inhibits the translation of a CatSper4 mRNA, by means of a small molecule that interferes with CatSper4 translation or post-translational processing, by means of a small molecule that interferes with CatSper4 localization, or by means of a molecule which blocks CatSper4 activity as an ion channel. Antibodies, including antibody fragments such as Fab fragments, F(ab')$_2$ fragments, Fv fragments, and single-chain Fv fragments (ScFv), also can be used to inhibit CatSper4 activity by binding to extracellular domains of the protein and thereby block its activity.

Because most repressors or antagonists of CatSper4 expression or activity will be reversible or will affect only mature sperm, the effects of such compounds on fertility will be reversible because the molecules will be cleared from the body over time and new sperm are constantly being produced. Thus, repressors or antagonists of CatSper4 expression or activity can be used as human contraceptives because they can cause reversible infertility. Such contraceptives can be taken orally or parenterally (e.g., injection, transdermal patch, or bioerodable implant) by females if they achieve sufficient concentrations in the vagina, uterus or fallopian tubes to effectively inhibit CatSper4 activity and thereby decrease sperm motility and the ability of sperm to penetrate the ZP. Similarly, such contraceptives can be taken orally or parenterally by males if they achieve sufficient concentration in the testes or seminal fluids to effectively inhibit CatSper4 expression or activity, and thereby decrease sperm motility and the ability of sperm to penetrate the ZP. Alternatively, such compounds can be formulated into lubricants, moisturizers, foams or jellies for use with prophylactics, cervical caps, or contraceptive vaginal sponges, foams or jellies.

In another series of embodiments, repressors or antagonists of CatSper4 genes and proteins can be used as contraceptives to treat non-human mammals. These embodiments are similar to those described above for human contraception. Such contraceptives can be used with respect to domesticated animals that are maintained as pets, with respect to other commercially valuable domesticated animals (e.g., cows, sheep, horses), or with respect to animal nuisances (e.g., mice, rats, raccoons, gophers). In some embodiments, the contraceptives are orally available and can be mixed into food sources for the animals. In other embodiments, the contraceptives can be administered parenterally (e.g., injection, transdermal patch, or bioerodable implant).

To the extent that the mammalian CatSper4 genes and proteins and the fish, amphibian and insect homologs of the CatSper4 genes and proteins share substantial sequence identity, repressors or antagonists of mammalian CatSper4 genes and proteins can also be used in the control of fish, amphibian and insect nuisances (e.g., mosquitoes). In addition, the non-mammalian homologs of the CatSper4 genes and proteins can be used to identify additional repressors and antagonists which are more specific or effective for such homologs.

Methods of CatSper4 Genotyping and Diagnosing CatSper4-Related Disorders.

In another aspect, the present invention provides methods for genotyping subjects with respect to the CatSper4 gene, and diagnosing CatSper4-related disorders such as infertility. Thus, for example, the CatSper4 nucleic acids (or a portion thereof) of a subject can be tested to ascertain whether that subject's CatSper4 genotype includes any mutations in the sequences relative to wild-type. Of particular significance would be mutations which introduce termination or frameshift mutations that prevent the production of functional CatSper4 proteins. Point mutations, however, can also be identified which cause decreased CatSper4 activity. Similarly, the antibodies of the present invention can be used to test the sperm of a subject to determine the presence or level of CatSper4 proteins. Of particular note would be an absence or significant decrease in the level of CatSper4 protein. Point mutations, however, can also cause infertility and can be detected by antibodies which are specific for epitopes including or affected by the mutant sequences. Determination of a subject's CatSper4 genotype can be used for genetic or reproductive counseling, or for diagnosing infertility that results from a CatSper4 defect.

To determine a subject's CatSper4 genotype, or for diagnosing a CatSper4-related disorder, the nucleic acids of the invention can be used as primers in polymerase chain reaction (PCR) (e.g., anchor PCR or RACE PCR), or ligase chain reaction (LCR) amplifications of the subject's DNA/mRNA. See, e.g., U.S. Pat. No. 4,683,195 and U.S. Pat. No. 4,683,202; Landegran et al. (1988), *Science* 241:1077-1080; Nakazawa et al. (1994), *Proc. Natl. Acad. Sci. USA* 91:360-364; and Abravaya et al. (1995), *Nucleic Acids Res.* 23:675-682. Other useful methods for amplifying a subjects DNA/mRNA using the nucleic acids of the invention include self-sustained sequence replication (e.g., Guatelli et al. (1990), *Proc. Natl. Acad. Sci. USA* 87:1874-1878), transcriptional amplification (e.g., Kwoh et al. (1989), *Proc. Natl. Acad. Sci. USA* 86:1173-1177), and Q-Beta Replicase-based systems (e.g., Lizardi et al. (1988), *Bio/Technology* 6:1197. The presence, absence or size of the resulting amplification products (e.g., Saiki et al. (1986), *Nature* 324:163; Saiki et al. (1989), *Proc. Natl. Acad. Sci. USA* 86:6230; Gibbs et al. (1989), *Nucleic Acids Res.* 17:2437-2448; Prossner (1993), *Tibtech* 11:238; Gasparini et al. (1992), *Mol. Cell Probes* 6:1; Barany (1991), *Proc. Natl. Acad. Sci. USA* 88:189), direct sequencing of the amplification products (e.g., Maxim and Gilbert (1977), *Proc. Natl. Acad. Sci. USA* 74:560; Sanger (1977), *Proc. Natl. Acad. Sci. USA* 74:5463), and other standard analytic techniques can be employed to determine CatSper4 genotypes. The amplified products can also be used in many of the techniques described below.

The nucleic acids of the invention also can be used as probes in hybridization and/or conformation-based assays to identify complementary or imperfectly complementary sequences in a subject.

For example, in some embodiments, mutations can be identified by selectively hybridizing sample nucleic acids to immobilized control nucleic acids. The controls can be adsorbed to filters or columns, or can be arranged in high density ordered arrays containing hundreds or thousands of oligonucleotides probes (see, e.g., Cronin et al. (1996), *Human Mutation* 7:244-255; Kozal et al. (1996), *Nature Medicine* 2:753-759).

In other embodiments, enzymatic or chemical cleavage can be employed to cleave or restrict duplexes of sample and control sequences at mismatched bases (e.g., Myers et al. (1985), *Science* 230:1242). For example, RNA/DNA duplexes can be treated with RNAse and DNA/DNA hybrids can be treated with 51 nuclease to digest duplexes at mismatched bases, G/A mismatches are cleaved at the A by the *E. coli* mutY enzyme, G/T mismatches are cleaved at the T by the human thymidine DNA glycosylase (see, e.g., Hsu et al. (1994), *Carcinogenesis* 15:1657-1662). Chemical cleavage of mismatches can be employed using, for example, hydroxylamine, osmium tetroxide and/or piperidine. See generally, e.g., Cotton et al. (1988), *Proc. Natl. Acad. Sci. USA* 85:4397; Saleeba et al. (1992), *Methods Enzymol.* 217:286-295; and U.S. Pat. No. 5,459,039.

In other embodiments, mutations can create or destroy specific sequences which serve cleavage points for restriction enzymes or ribozymes. Thus, restriction fragment length polymorphism (RFLP) analysis can be employed in which (amplified) sample DNA is digested with at least one restriction endonuclease, and the resulting fragment lengths are analyzed and compared to controls to determine the presence or absence of mutations which affect the pattern of restriction fragment lengths. Similarly, sequence-specific ribozymes can be used to identify mutations that create or destroy ribozyme cleavage sites. See, e.g., U.S. Pat. No. 5,498,531.

In other embodiments, mutations can be detected by their effect on the electrophoretic mobility of a sequence, either as a single-stranded nucleic acid or as duplex. For example, single-strand conformation polymorphism (SSCP) analysis (Orita et al. (1989), *Proc. Natl. Acad. Sci. USA* 86:2766; Cotton (1993), *Mutat. Res.* 285:125-144; Hayashi (1992), *Genet. Anal. Tech. Appl.* 9:73-79; and Keen et al. (1991), *Trends Genet.* 7:5). denaturing gradient gel electrophoresis (DGGE) (Myers et al. (1985), *Nature* 313:495). and temperature gradient gel electrophoresis (Rosenbaum and Reissner (1987), *Biophys. Chem.* 265:12753) can be employed.

These and other methods of detecting mutations in the CatSper4 genes and proteins will be apparent to one of ordinary skill in the art based upon the nucleic acid and protein sequences disclosed herein.

In Vitro Fertilization.

In another aspect, the present invention provides a method of in vitro fertilization of ova by sperm characterized by decreased CatSper4 expression or activity. It has previously been shown that CatSper1-deficient sperm appear to be normal in all respects except in their motility and their ability to penetrate the ZP. Moreover, CatSper1-deficient sperm are capable of fertilizing ova from which the ZP has been removed. It is expected that CatSper4-deficient sperm will have similarly reduced motility and ability to fertilize ova with intact ZPs. Thus, the present invention provides a method of in vitro fertilization for CatSper4-deficient males in which the sperms of such males are treated to overcome the CatSper4 deficiency or are contacted with ova from which the ZP have been removed. Because other genetic deficiencies can result in sperm which are incapable of penetrating the ZP, this method can be extended to other males having genetic deficiencies which affect ZP-penetration or for which in vitro fertilization previously has been unsuccessful using ova with intact ZPs.

Methods of Treating CatSper4-Mediated Infertility.

In another aspect, the present invention provides methods of treating infertility in CatSper4-deficient males, in which an enhancer of CatSper4 expression or an agonist of CatSper4 activity is administered to the subject. In other embodiments, gene or protein therapy can be employed to provide the CatSper4 gene or protein to sperm (or sperm progenitors) which are deficient in the CatSper4 gene or protein. For gene therapy, a genetic construct encoding a CatSper4 protein can be employed to cause expression of a CatSper4 protein in sperm or sperm progenitors which are deficient in the CatSper4 gene or protein.

In another aspect, infertility of a mating pair (e.g., a human couple) can result from antibodies generated by the female against antigens present on the sperm of the male. In some cases, the antibodies can be directed against an epitope of a CatSper4 protein. Thus, the present invention also provides methods of diagnosing an anti-CatSper4 antibody-mediated infertility caused by anti-CatSper4 antibodies present in a female urogenital tract. The methods include obtaining a sample of antibodies present in the female and contacting the antibodies with CatSper4 proteins or fragments of CatSper4 proteins. In some embodiments, the CatSper4 fragments are epitopes of the CatSper4 proteins having high predicted antigenicity (e.g., a high predicted antigenicity epitope of SEQ ID NO: 2, or a high predicted antigenicity epitope of SEQ ID NO: 4, and allelic and mammalian homologs thereof). In these methods, either the female's antibodies or the CatSper4 proteins/fragments optionally can be immobilized and either the female's antibodies or the CatSper4 proteins/fragments optionally can be detectably labeled to facilitate detection of binding between the antibodies and the CatSper4 proteins/fragments.

In these cases, administering an excess of the CatSper4 protein, or at least a fragment of the CatSper4 protein including the relevant epitope, can saturate the binding sites of the anti-CatSper4 antibodies present in the female's urogenital tract and thereby inhibit or reduce the antibody-mediated infertility. Alternatively, an anti-idiotypic antibody (i.e., an antibody which specifically binds to the variable regions of another antibody with a defined specificity) can be employed. That is, an antibody which binds specifically to anti-CatSper4 antibodies can be employed to inhibit the anti-CatSper4 antibodies present in the female's urogenital tract and thereby inhibit or reduce the antibody-mediated infertility. One of ordinary skill in the art can easily identify the relevant CatSper4 epitopes recognized by such female antibodies (e.g., using the methods described above) and produce substantially pure preparations of the relevant epitope or anti-idiotypic antibodies by standard means. Thus, the invention also provides methods for treating an anti-CatSper4 antibody-mediated infertility caused by anti-CatSper4 antibodies present in a female urogenital tract. The methods include administering into the urogenital tract of the female an amount of the relevant CatSper4 epitope (or whole CatSper4 protein) or an amount an anti-idiotypic antibody effective to inhibit the anti-CatSper4 antibodies and thereby inhibit or reduce the antibody-mediated infertility.

Business Methods Relating to CatSper4.

In another aspect, the present invention provides a method of conducting a drug discovery business comprising: identifying, by the assays of the invention, one or more agents which antagonize CatSper4 activity; determining if an agent identified in such an assay, or an analog of such an agent, inhibits at least one of sperm motility or egg penetrance; conducting therapeutic profiling of an agent identified as an antagonist for efficacy and toxicity in one or more animal models; and formulating a pharmaceutical preparation including one or more antagonist agents identified as having an acceptable therapeutic profile.

In one embodiment, the drug discovery business further includes the step of establishing a system for distributing the pharmaceutical preparation for sale, and can optionally include establishing a sales group for marketing the pharmaceutical preparation.

In another aspect, the present invention provides a method of conducting a drug discovery business comprising: identifying, by the subject assay, one or more agents which agonize CatSper4 activity; determining if an agent identified in such an assay, or an analog of such an agent, increases at least one of sperm motility or egg penetrance; conducting therapeutic profiling of an agent identified as an agonist for efficacy and toxicity in one or more animal models; and formulating a pharmaceutical preparation including one or more agents identified as having an acceptable therapeutic profile.

In certain embodiments, the drug discovery business further includes the step of establishing a system for distributing the pharmaceutical preparation for sale, and can optionally include establishing a sales group for marketing the pharmaceutical preparation.

In certain embodiments, the assay to identify agents which agonize CatSper4 activity is conducted using wild type CatSper4. In another embodiment, the assay to identify agents which agonize CatSper4 activity is conducted using a mutant CatSper4. By a mutant CatSper4 is meant to include a CatSper4 polypeptide containing one or more insertions, deletions, or substitutions in amino acid sequence, wherein said insertions, deletions, or substitutions change the activity of the mutant CatSper4 in comparison to wild type CatSper4. Such a change in activity includes, but is not limited to, a change in motility, egg penetrance, cation transport. A change in activity would also include a change in the proper localization or expression of the CatSper4 protein or mRNA.

In still another aspect, the invention provides a method of conducting a reproductive medicine business comprising: examining a sperm sample from a male patient, wherein said patient is experiencing a fertility problem; determining if said sperm are characterized by at least one of a decrease in motility or a decrease in egg penetrance; performing in vitro analysis to determine the efficacy of a CatSper4 agonist in increasing at least one of sperm motility or egg penetrance; establishing a treatment regimen comprising administering an amount of a CatSper4 agonist effective to increase at least one of sperm motility or egg penetrance in said male.

In certain embodiments, the method further includes a step wherein said male patient is monitored by a physician to evaluate improvement in fertility. Such evaluation can include examination of sperm at regular intervals following the initiation of treatment to measure improvements in one or more of sperm motility or egg penetrance. The frequency of follow-up evaluation by the treating physician will be determined by the physician or a trained health care provider. Factors to consider are the patient's schedule and comfort level, as well as the urgency with which a male patient is attempting to father an offspring. Representative follow-up appointments can be conducted weekly, semi-weekly, or monthly. In another embodiment, the method further includes the step of billing the patient or the patient's insurance provider. We note that in cases where the patient's health insurance is paying for all or a portion of said fertility treatments, the policies of said health insurance provider will likely influence the frequency of follow-up appointments.

In yet another aspect, the present invention provides a method of conducting a contraceptive medicine business comprising: providing a pharmaceutical preparation discovered through the methods of a drug discovery business, wherein said preparation inhibits the activity of CatSper4; providing instructions to physicians and health care providers for the administration of an amount of said pharmaceutical preparation effective to inhibit the activity of CatSper4, wherein said effective amount is sufficient to prevent pregnancy.

In one embodiment, the method further includes the step of establishing a system for distributing the pharmaceutical preparation for sale, and can optionally include establishing a sales group for marketing the pharmaceutical preparation.

CatSper4 encodes a cation channel. Numerous types of cation channels play critical roles in cellular processes including regulation of cardiac function (e.g., calcium channels). Thus, a great limitation of methods which employ administration of agents which either increase or decrease the activity of cation channels is that such methods are likely to have substantial side-effects. These side-effects can include significant cardiac complications. However, as disclosed herein, CatSper4 is specifically expressed in sperm. Accordingly, agents which increase or decrease the activity of CatSper4 can be administered to patients without the side effects associated with either general cation channel antagonists and agonists, or antagonists and agonists of cation channels which are more widely expressed in the body.

Through a drug discovery business, one or more agents which can antagonize the activity of CatSper4 can be identified. By antagonize the activity is meant to decrease, in whole or in part, the activity of CatSper4. Such a decrease in activity can be measured by examining at least one of sperm motility, egg penetrance, or cation transport. The terms decrease and antagonize will be used interchangeably throughout.

In certain embodiments, the initially identified CatSper4 agonist or antagonist can be subjected to further lead optimization, e.g., to further refine the structure of a lead compound so that potency and activity are maintained but balanced with important pharmacological characteristics including:
  Solubility
  Permeability
  Bioavailability
  Toxicity
  Mutagenicity
  Pharmacokinetics—absorption, distribution, metabolism, elimination of the drug Structural modifications are made to a lead compound to address issues with the parameters listed above. These modifications however, must take into account possible effects on the molecule's potency and activity. For example, if the solubility of a lead compound is poor, changes can be made to the molecule in an effort to improve solubility; these modifications, however, can negatively affect the molecule's potency and activity. SAR data are then used to determine the effect of the change upon potency and activity. Using an iterative process of structural modifications and SAR data, a balance is created between these pharmacological parameters and the potency and activity of the compound.

Candidate antagonists, or combinations thereof, must them be tested for efficacy and toxicity in animal models. Such therapeutic profiling is commonly employed in the pharmaceutical arts. Before testing an experimental drug in humans, extensive therapeutic profiling (e.g., preclinical testing) must be completed to establish initial parameters for safety and efficacy. Preclinical testing establishes a mechanism of action for the drug, its bioavailability, absorption, distribution, metabolism, and elimination through studies performed in vitro (that is, in test tubes, beakers, petri dishes, etc.) and in animals. Animal studies are used to assess whether the drug will provide the desired results. Varying doses of the experimental drug are administered to test the drug's efficacy, identify harmful side-effects that may occur, and evaluate toxicity.

Briefly, one of skill in the art will recognize that the identification of a candidate agent which antagonizes CatSper4 activity in a drug based screen is a first step in developing a pharmaceutical preparation useful as a contraceptive agent. Administration of an amount of said pharmaceutical preparation effective to successfully prevent pregnancy (i.e., to act as a useful contraceptive agent) must be both safe and effective. Early stage drug trials, routinely used in the art, help to address concerns of the safety and efficacy of a potential pharmaceutical. In the specific case of a CatSper4 antagonist, efficacy of the pharmaceutical preparation could be readily evaluated in a mouse or rat model. Briefly, male mice could be administered varying doses of said pharmaceutical preparations over various time schedules. Control male mice can be administered a placebo (e.g., carrier or excipient alone). The male mice are then allowed to mate freely by placing said male into cages with female mice, and measuring rate of conception over time. Given the efficacy of currently available forms of birth control, an effective contraception should be at least 80% effective, preferably 85% effective, more preferably 90% effective, most preferably 95%, 96%, 97%, 98%, 99% or greater than 99% effective in preventing pregnancy.

In one embodiment, the step of therapeutic profiling includes toxicity testing of compounds in cell cultures and in animals; analysis of pharmacokinetics and metabolism of the candidate drug; and determination of efficacy in animal models of diseases. In certain instances, the method can include analyzing structure-activity relationship and optimizing lead structures based on efficacy, safety and pharmacokinetic profiles. The goal of such steps is the selection of drug candidates for pre-clinical studies to lead to filing of Investigational New Drug ("IND") applications with the U.S. FDA and/or similar applications with similar regulatory authorities prior to human clinical trials.

Between lead optimization and therapeutic profiling, one goal of the subject method is to develop a CatSper4 agonist or antagonist which has minimal side-effects. In the case of antagonists, the lead compounds will have clinically acceptable effects on vasodilatation (i.e., dizziness, hypotension, headache, flushing, edema, etc.), myocardial ischemia, hypotension, bradycardia, transient asystole, exacerbation of heart failure, ventricular dysfunction, SA node or AV conduction disturbances, or plasma digoxin levels.

By "toxicity profiling" is meant the evaluation of potentially harmful side-effects which may occur when an effective amount of a pharmaceutical preparation is administered. A side-effect may or may not be harmful, and the determination of whether a side effect associated with a pharmaceutical preparation is an acceptable side effect is made during the regulatory approval process. This determination does not follow hard and fast rules, and that which is considered an acceptable side effect varies due to factors including: (a) the severity of the condition being treated, and (b) the availability of other treatments and the side-effects currently associated with these available treatments. For example, the term cancer encompasses a complex family of disease states related to mis-regulated cell growth, proliferation, and differentiation. Many forms of cancer are particularly devastating diseases which cause severe pain, loss of function of the effected tissue, and death. Chemotherapeutic drugs are an important part of the standard therapy for many forms of cancer. Although chemotherapeutics themselves can have serious side-effects including hair-loss, severe nausea, weight-loss, and sterility, such side-effects are considered acceptable given the severity of the disease they aim to treat.

In contrast, however, most currently available forms of birth control do not have significant side-effects. Thus, a pharmaceutical preparation of a CatSper4 antagonist should have minimal toxicity and side-effects. Toxicity tests can be conducted in tandem with efficacy tests, and male mice administered effective doses of the pharmaceutical preparation can be monitored for adverse reactions to the preparation. Potential adverse reactions associated with a contraceptive agent may include loss of sex drive and behavioral changes. Blood, urine, and fecal samples taken from treated mice can also be monitored to detect any potential adverse changes in immune, kidney, or liver function. Additionally, given that CatSper4 is a cation channel, mice receiving said pharmaceutical preparation should also be monitored for any changes in cardiac function indicative of cross reactivity of the CatSper4 antagonist with other cation channels.

Agents which antagonize CatSper4 activity, and which are proven safe and effective in animal studies, can be formulated into a pharmaceutical preparation. Such pharmaceutical preparations can then be marketed, distributed, and sold as contraceptive agents.

Given the link between loss of CatSper4 activity and fertility, there is substantial utility in agents which increase the activity of CatSper4 to treat male fertility problems. Many instances of infertility involve problems linked to the male. Such male infertility issues include low sperm count, poor sperm motility, and abnormal sperm morphology. Currently there are few effective treatments for male-associated infertility.

The first step in developing potentially successful treatments for male infertility is the identification of CatSper4 agonists. A CatSper4 agonist is one or more agents which increase the activity of CatSper4. As explained above with respect to CatSper4 antagonists, agonists of the CatSper4 protein are also expected to have fewer potential side-effects than other cation channel agonists.

Methods for identifying agents which act as CatSper4 agonists are performed largely as detailed for CatSper4 antagonists. However, a preferred CatSper4 agonist will increase one or more of sperm motility or egg penetrance. Additionally, we note that when identifying a CatSper4 agonist, such an agent can agonize the activity of a wild type CatSper4. In addition, or alternatively, such an agent can agonize the activity of a mutant CatSper4. One or more agonists identified by these methods can then be tested for safety and efficacy, as outline in detail above. Agents which are shown to be safe and effective in animal studies are formulated into a pharmaceutical preparation.

We note that said CatSper4 agonists are not likely to be effective for treating all male fertility problems. However, it is expected that some undetermined percentage of male fertility problems will be amenable to treatment using agonists of CatSper4 function. For example, a certain percentage of male infertility which results in poor sperm motility is likely due to mutations in CatSper4. Given that CatSper4 is expressed specifically in sperm, males possessing such a mutation would be expected to have little or no additional medical problems, and this explains in part why infertility is often found in otherwise healthy men. Additionally, a CatSper4 agonist can improve sperm motility overall, and thus help compensate for poor sperm motility due to other unrelated causes.

Conducting a Reproductive Medicine Business.

A pharmaceutical preparation including one or more agents which agonize the activity of a wild type or mutant CatSper4 can be useful in establishing a reproductive medicine business which provides treatment for candidate male patients experiencing fertility difficulties. Sperm samples provided by male patients are examined to determine if infertility in said male patients may be amenable to treatment with the pharmaceutical preparation. Patients whose sperm is characterized by a decrease in at least one of motility or egg penetrance may be eligible for treatment. Prior to treatment, sperm samples provided by the male patients are tested in vitro with the pharmaceutical preparation to further assess whether said male is eligible for treatment. This additional step of in vitro testing helps to alleviate unnecessary treatment in males whose infertility is unlikely to be improved with the CatSper4 agonist.

Male patients whose sperm shows increased motility or egg penetrance in vitro are eligible for fertility treatment including the pharmaceutical preparation including one or more CatSper4 agonist. The exact treatment regimen will vary from patient to patient, and can be readily determined by an experienced medical professional. However, the treatment regimen will include administration of an amount of said pharmaceutical preparation effective to increase at least one of sperm motility or egg penetrance in said treated male. In a preferred embodiment, the increase in sperm motility or egg penetrance will result in an increase in fertility.

Pharmaceutical Preparations.

Pharmaceutically acceptable preparations comprising a therapeutically effective amount of one or more of the identified agents (i.e., antagonists or agonists) described above, formulated together with one or more pharmaceutically acceptable carriers (additives) and/or diluents. As described in detail below, the pharmaceutical compositions of the present invention can be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds can be simply dissolved or suspended in sterile water.

The phrase "therapeutically effective amount" as used herein means that amount of an agent or composition which is effective for producing some desired therapeutic effect, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject antagonists from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, the pharmaceutical preparation is non-pyrogenic, i.e., does not elevate the body temperature of a patient.

The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977), *J. Pharm. Sci.* 66: 1-19.)

The pharmaceutically acceptable salts of the subject agents include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the agents of the present invention can contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the agents, or by separately reacting the purified agent in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al. (1977), supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations can conveniently be presented in unit dosage form and can be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1% to about 99% of active ingredient, preferably from about 5% to about 70%, most preferably from about 10% to about 30%.

Methods of preparing these formulations or compositions include the step of bringing into association one or more agents of the present invention with the carrier and, optionally, one or more accessory ingredients. In general, the formulations are prepared by uniformly and intimately bringing into association one or more agents of the present invention with liquid carriers, or finely divided solid carriers, or both, and then, if necessary, shaping the product.

Formulations of the invention suitable for oral administration can be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A agent of the present invention can also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions can also comprise buffering agents. Solid compositions of a similar type can also be employed as fillers in soft and hard-filled gelatin capsules using such excipients as lactose or milk sugars, as well as high molecular weight polyethylene glycols and the like.

A tablet can be made by compression or molding, optionally with one or more accessory ingredients. Compressed tablets can be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets can be made by molding in a suitable machine a mixture of the powdered compound moistened with an inert liquid diluent.

The tablets, and other solid dosage forms of the pharmaceutical compositions of the present invention, such as dragees, capsules, pills and granules, can optionally be scored or prepared with coatings and shells, such as enteric coatings and other coatings well known in the pharmaceutical-formulating art. They can also be formulated so as to provide slow or controlled release of the active ingredient therein using, for example, hydroxypropylmethyl cellulose in varying proportions to provide the desired release profile, other polymer matrices, liposomes and/or microspheres. They can be sterilized by, for example, filtration through a bacteria-retaining filter, or by incorporating sterilizing agents in the form of sterile solid compositions which can be dissolved in sterile water, or some other sterile injectable medium immediately before use. These compositions can also optionally contain opacifying agents and can be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms can contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration can be presented as a suppository, which can be prepared by mixing one or more agents of the invention with one or more suitable non-irritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of one or more agents of this invention include powders, sprays, ointments, pastes, creams, lotions, gels, solutions, patches and inhalants. The active agents can be mixed under sterile conditions with a pharmaceutically acceptable carrier, and with any preservatives, buffers, or propellants which can be required.

The ointments, pastes, creams and gels can contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of an agent of the present invention to the body. Such dosage forms can be made by dissolving or dispersing the subject compound in the proper medium. Absorption enhancers can also be used to increase the flux of the subject agent across the skin. The rate of such flux can be controlled by either providing a rate controlling membrane or dispersing the compound in a polymer matrix or gel.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which can be reconstituted into sterile injectable solutions or dispersions just prior to use, which can contain antioxidants, buffers, bacteriostats, solutes which render the formulation isotonic with the blood of the intended recipient or suspending or thickening agents.

Examples of suitable aqueous and nonaqueous carriers which can be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

EQUIVALENTS

While this invention has been particularly shown and described with references to preferred embodiments thereof, it will be understood by those skilled in the art that various changes in form and details may be made therein without departing from the spirit and scope of the invention. Those skilled in the art will recognize, or be able to ascertain using no more than routine experimentation, many equivalents to the specific embodiments of the invention described specifically herein. Such equivalents are intended to be encompassed in the scope of the invention.

We claim:

1. A method of identifying a compound having potential contraceptive activity, the method comprising:
   (a) contacting a candidate compound with a cell expressing a CatSper4 protein, the CatSper4 protein comprising at least 90% similarity to the amino acid sequence of SEQ ID NO: 2, and wherein the CatSper4 protein has CatSper4 activity;
   (b) measuring an indicator of CatSper4 activity in the cell, wherein the indicator is cation flux across a membrane of the cell, whole cell currents of the cell, or channel currents of the cell;
   (c) determining whether the candidate compound caused a decrease in CatSper4 activity in the cell relative to CatSper4 activity prior to contact with the candidate compound;
   (d) toxicity profiling the candidate compound; and
   (e) identifying the candidate compound as having potential contraceptive activity if a decrease is determined in (c) and if acceptable toxicity and side effects determined in (d).

2. The method as in claim 1, wherein toxicity profiling is performed in an animal.

3. The method as in claim 2, wherein toxicity profiling is performed by monitoring the animal for adverse changes in at least one of immune function, kidney function, liver function, and cardiac function.

4. A method of identifying a compound that inhibits sperm motility, the method comprising:
   (a) contacting a candidate compound with a cell that has been transformed with a genetic construct capable of expressing a CatSper4 protein, the CatSper4 protein comprising at least 90% similarity to the amino acid sequence of SEQ ID NO: 2, and wherein the CatSper4 protein has CatSper4 activity;
   (b) measuring an indicator of CatSper4 activity in the cell, wherein the indicator is cation flux across a membrane of the cell, whole cell currents of the cell, or channel currents of the cell;
   (c) determining whether the candidate compound caused a decrease in CatSper4 activity in the cell relative to a level of CatSper4 activity prior to contact with the candidate compound;
   (d) toxicity profiling the candidate compound;
   (e) contacting the candidate compound with normal sperm if the candidate compound causes a decrease in CatSper4 activity in the cell; and
   (f) identifying the candidate compound as inhibiting sperm motility if it causes a decrease in sperm motility and if acceptable toxicity and side effects are determined.

5. A method of selecting one or more potential male contraceptives from a library of candidate compounds, the method comprising:
   (a) contacting a cell expressing a CatSper4 protein with at least one candidate compound from the library, the CatSper4 protein comprising at least 90% similarity to the amino acid sequence of SEQ ID NO: 2, and wherein the CatSper4 protein has CatSper4 activity;

(b) measuring an indicator of CatSper4 activity in the cell, wherein the indicator is cation flux across a membrane of the cell, whole cell currents of the cell, or channel currents of the cell;

(c) determining whether the step of contacting caused a decrease in CatSper4 activity in the cell relative to CatSper4 activity prior to contact with the candidate compound;

(d) toxicity profiling the candidate compound;

(e) contacting said candidate compound with normal sperm if said candidate compound causes a decrease in CatSper4 activity in the cell; and (f) selecting said candidate compound as a potential male contraceptive if it causes a decrease in sperm motility and if acceptable toxicity and side effects are determined.

6. A method of identifying a compound having potential contraceptive activity, the method comprising:

(a) contacting normal sperm with a candidate compound previously identified as causing a decrease in CatSper4 protein activity in a cell and having acceptable toxicity and side effects, the CatSper4 protein comprising at least 90% similarity to the amino acid sequence of SEQ ID NO: 2, and wherein the CatSper4 protein has CatSper4 activity;

(b) assaying for an increase or decrease in sperm motility relative to Sperm motility in the cell prior to contact with the candidate compound; and (c) identifying said candidate compound as having potential contraceptive activity if it causes a decrease in sperm motility.

7. The method of claim 6, wherein said candidate compound was previously identified as causing a decrease in CatSper4 activity in a cell and having acceptable toxicity and side effects by the steps comprising:

(1) contacting a candidate compound with a cell expressing a CatSper4 protein, the CatSper4 protein comprising at least 90% similarity to the amino acid sequence of SEQ ID NO: 2, and wherein the CatSper4 protein has CatSper4 activity;

(2) measuring an indicator of CatSper4 expression or activity in the cell, wherein the indicator is cation flux across a membrane of the cell, whole cell currents of the cell, or channel currents of the cell;

(3) determining whether the candidate compound caused a decrease in CatSper4 activity in the cell relative to CatSper4 activity prior to contact with the candidate compound;

(4) toxicity profiling the candidate compound; and (5) identifying the candidate compound as causing a decrease in CatSper4 activity in a cell and having acceptable toxicity and side effects.

8. A method of identifying a compound that inhibits sperm motility, the method comprising:

(a) contacting normal sperm with a candidate compound previously identified as causing a decrease in CatSper4 activity in a cell and having acceptable toxicity and side effects, the CatSper4 protein comprising at least 90% similarity to the amino acid sequence of SEQ ID NO: 2, and wherein the CatSper4 protein has CatSper4 activity;

(b) assaying for an increase or decrease in sperm motility relative to sperm motility in the cell prior to contact with the candidate compound; and (c) identifying said compound as inhibiting sperm motility if it causes a decrease in sperm motility.

9. The method of claim 8, wherein said candidate compound was previously identified as causing a decrease in CatSper4 activity in a cell and having acceptable toxicity and side effects by the steps comprising:

(1) contacting a candidate compound with a cell that has been transformed with a genetic construct capable of expressing a CatSper 4 protein, the CatSper4 protein comprising at least 90% similarity to the amino acid sequence of SEQ ID NO: 2, and wherein the CatSper4 protein has CatSper4 activity;

(2) measuring an indicator of CatSper4 activity in the cell;

(3) determining whether the candidate compound caused a decrease in CatSper4 activity in the cell relative to CatSper4 activity prior to contact with the candidate compound;

(4) toxicity profiling the candidate compound; and (5) identifying the candidate compound as causing a decrease in CatSper4 activity in a cell and having acceptable toxicity and side effects.

10. A method of selecting one or more potential male contraceptives from a library of candidate compounds, the method comprising:

(a) contacting normal sperm with a candidate compound previously identified as causing a decrease in CatSper4 activity in a cell and having acceptable toxicity and side effects, the CatSper4 protein comprising at least 90% similarity to the amino acid sequence of SEQ ID NO: 2, and wherein the CatSper4 protein has CatSper4 activity;

(b) assaying for an increase or decrease in sperm motility relative to sperm motility in the cell prior to contact with the candidate compound;

(c) identifying said compound as having potential contraceptive activity if it causes a decrease in sperm motility; and (d) selecting said compound as a potential male contraceptive.

11. The method of claim 10, wherein said candidate compound was previously identified as causing a decrease in CatSper4 activity in a cell by the steps comprising:

(1) contacting a cell expressing a CatSper4 protein with at least one candidate compound from a library, the CatSper4 protein comprising at least 90% similarity to the amino acid sequence of SEQ ID NO: 2, and wherein the CatSper4 protein has CatSper4 activity;

(2) measuring an indicator of CatSper4 activity in the cell;

(3) determining whether the candidate compound caused a decrease in CatSper4 activity in the cell relative to CatSper4 activity prior to contact with the candidate compound; and (4) identifying the candidate compound from the library as causing a decrease in CatSper4 activity in the cell.

* * * * *

SEQUENCE LISTING

<160> NUMBER OF SEQ ID NOS: 7

<210> SEQ ID NO 1
<211> LENGTH: 1197
<212> TYPE: DNA
<213> ORGANISM: Homo sapiens

<400> SEQUENCE: 1

```
atgtctcaac accgtcacca gcgccactcg agagtcattt ctagttcacc agttgacact      60
acatcggtgg gattttgccc aacattcaag aaatttaaga ggaacgatga tgaatgtcgg     120
gcatttgtga agagagtcat aatgagccgt ttctttaaga taattatgat tagcactgtc     180
acatcgaatg cgttttttat ggccttgtgg accagttatg acataaggta ccgcttgttc     240
agacttcttg agttctcgga gatcttcttt gtgtccatct gcacatctga gttgtccatg     300
aaggtctatg tggaccccat caactactgg aagaacggct acaacctgct ggatgtgatc     360
attatcatcg ttatgttttt accctatgcc ctccgccagc tcatgggcaa acagttcact     420
tacctgtata tcgctgatgg catgcagtcc ctgcgcatcc tcaagcttat cggctatagc     480
cagggcatcc ggacgctgat caccgccgtg gggcagacag tctacaccgt ggcctctgtg     540
ctcctcctgc tcttcctcct catgtacatc ttcgctatct tgggcttctg cctgtttgga     600
tctccagaca atggtgacca tgataactgg gggaacctgg ctgcagcttt tttcacccte     660 ttcagcttgg ccacggttga tggctggaca gacctgcaga agcagttgga caatcgggaa     720 tttgcttga gccgggcatt caccatcatc ttcatcttgc tcgcctcttt catcttcctc     780
aacatgttcg tgggtgtgat gatcatgcac acagaggact ccatcagaaa gtttgagcga     840
gagctgatgt tggagcagca ggagatgctc atgggagaga agcaggtgat tctgcagcgg     900
cagcaggagg agatcagcag gctgatgcac atacagaaaa atgctgactg cacaagtttc     960
agtgagctgg tggagaactt taagaagacc ttgagccaca ctgacccaat ggtcttggat    1020
gattttggca ctagcttacc cttcatcgat atctactttt ccactctgga ctaccaggac    1080
acaactgtcc acaagcttca agagctgtac tatgagatcg tgcatgtgct gagcctaatg    1140
ctggaagact gccccagga gaagcccag tccttggaaa aggtggatga gaagtag        1197
```

<210> SEQ ID NO 2
<211> LENGTH: 398
<212> TYPE: PRT
<213> ORGANISM: Homo sapiens

<400> SEQUENCE: 2

```
Met Ser Gln His Arg His Gln Arg His Ser Arg Val Ile Ser Ser Ser
1               5                  10                  15

Pro Val Asp Thr Thr Ser Val Gly Phe Cys Pro Thr Phe Lys Lys Phe
            20                  25                  30

Lys Arg Asn Asp Asp Glu Cys Arg Ala Phe Val Lys Arg Val Ile Met
        35                  40                  45

Ser Arg Phe Phe Lys Ile Ile Met Ile Ser Thr Val Thr Ser Asn Ala
```

```
                50                  55                  60
Phe Phe Met Ala Leu Trp Thr Ser Tyr Asp Ile Arg Tyr Arg Leu Phe
 65                  70                  75                  80

Arg Leu Leu Glu Phe Ser Glu Ile Phe Val Ser Ile Cys Thr Ser
                 85                  90                  95

Glu Leu Ser Met Lys Val Tyr Val Asp Pro Ile Asn Tyr Trp Lys Asn
                100                 105                 110

Gly Tyr Asn Leu Leu Asp Val Ile Ile Ile Val Met Phe Leu Pro
            115                 120                 125

Tyr Ala Leu Arg Gln Leu Met Gly Lys Gln Phe Thr Tyr Leu Tyr Ile
130                 135                 140

Ala Asp Gly Met Gln Ser Leu Arg Ile Leu Lys Leu Ile Gly Tyr Ser
145                 150                 155                 160

Gln Gly Ile Arg Thr Leu Ile Thr Ala Val Gly Gln Thr Val Tyr Thr
                165                 170                 175

Val Ala Ser Val Leu Leu Leu Phe Leu Leu Met Tyr Ile Phe Ala
            180                 185                 190

Ile Leu Gly Phe Cys Leu Phe Gly Ser Pro Asp Asn Gly Asp His Asp
                195                 200                 205

Asn Trp Gly Asn Leu Ala Ala Ala Phe Phe Thr Leu Phe Ser Leu Ala
210                 215                 220

Thr Val Asp Gly Trp Thr Asp Leu Gln Lys Gln Leu Asp Asn Arg Glu
225                 230                 235                 240

Phe Ala Leu Ser Arg Ala Phe Thr Ile Ile Phe Ile Leu Leu Ala Ser
                245                 250                 255

Phe Ile Phe Leu Asn Met Phe Val Gly Val Met Ile Met His Thr Glu
                260                 265                 270

Asp Ser Ile Arg Lys Phe Glu Arg Glu Leu Met Leu Glu Gln Gln Glu
                275                 280                 285

Met Leu Met Gly Glu Lys Gln Val Ile Leu Gln Arg Gln Gln Glu Glu
290                 295                 300

Ile Ser Arg Leu Met His Ile Gln Lys Asn Ala Asp Cys Thr Ser Phe
305                 310                 315                 320

Ser Glu Leu Val Glu Asn Phe Lys Lys Thr Leu Ser His Thr Asp Pro
                325                 330                 335

Met Val Leu Asp Asp Phe Gly Thr Ser Leu Pro Phe Ile Asp Ile Tyr
            340                 345                 350

Phe Ser Thr Leu Asp Tyr Gln Asp Thr Thr Val His Lys Leu Gln Glu
                355                 360                 365

Leu Tyr Tyr Glu Ile Val His Val Leu Ser Leu Met Leu Glu Asp Leu
            370                 375                 380

Pro Gln Glu Lys Pro Gln Ser Leu Glu Lys Val Asp Glu Lys
385                 390                 395

<210> SEQ ID NO 3
<211> LENGTH: 1188
<212> TYPE: DNA
<213> ORGANISM: Mus musculus

<400> SEQUENCE: 3
atgtcccaac atttttcacca caaccctgta cgagtcaagt cgggctcact gtttgctaca       60
gcatcggaag cattgcaggc aagactgagc aagattaaga ggaaggataa ggagtgccag      120
gcttacttca ggaaggttat taagagcact ttcttccaga ttgtgatgat caccacggtc      180
```

```
accaccaact cctttttact ggtcttgggg actaattatg acatacaatt cgagttttc      240 agaacctttg aggtctcaga gcttttcttt gtatctgtct atgtctgcga gttcctcatg      300
aaggtctatg tggaccccat tacatactgg aaggatggct ataacatact ggatgtgatc      360
attctcatca ttctcaccat accctatctc ctccgcaaaa tcaaggggaa tcattctgca      420
tacctccact tgctgatgg catccagtct ctacgaatcc tcaagcttat ctcctacagt       480
aggggcatca ggacactcat catcgctgtg ggggagacgg tctacactgt ggcctcggtg      540
ctgacgctgc tcttcctcct catgtttgtg ttcgcgatcc tgggattctg cctatttggc      600
gtgacggaca gaggcgacct ggagaactgg gggaacctgg cttcagcttt ctttactctc      660
ttcagtttgg ccacggttga tggctggact gacctgcagg aagagctgga caagaggaag      720
tttactgtga gccgggcgtt tactatcctc ttcatcttgc ttgcatcctt catcttcctc      780
aacatgtttg tgggtgtgat gatcatgcac acggaggatt ccatgaaaaa gtttgagcgg      840
gatctgacgt ggagaggaa ccttgcgatt atggaggaga agcaaataat cctgaaacgc       900
cagcaagagg aggtcaacag gctgatgaac acacagaaaa ctggtagcat gaacttcatt      960
gatatggtgg agggcttcaa gaagaccctg cggcacacag accccatggt tctggatgac     1020
ttcagcacta gtctctcctt cattgatatc tacttggtca cactggacaa ccaagatgtt     1080
attgtcagca agcttcagga gctctactgt gagattgtga acgtgctgag cctgatgttg     1140
gaagacatgc ccaaggagag ctcgtccagc ctctcgggac taagttaa                  1188

<210> SEQ ID NO 4
<211> LENGTH: 395
<212> TYPE: PRT
<213> ORGANISM: Mus musculus

<400> SEQUENCE: 4

Met Ser Gln His Phe His His Asn Pro Val Arg Val Lys Ser Gly Ser
1               5                   10                  15

Leu Phe Ala Thr Ala Ser Glu Ala Leu Gln Ala Arg Leu Ser Lys Ile
            20                  25                  30

Lys Arg Lys Asp Lys Glu Cys Gln Ala Tyr Phe Arg Lys Val Ile Lys
        35                  40                  45

Ser Thr Phe Phe Gln Ile Val Met Ile Thr Thr Val Thr Thr Asn Ser
    50                  55                  60

Phe Leu Leu Val Leu Gly Thr Asn Tyr Asp Ile Gln Phe Glu Phe Phe
65                  70                  75                  80

Arg Thr Phe Glu Phe Val Ser Glu Leu Phe Phe Val Ser Val Tyr Val
                85                  90                  95

Cys Glu Leu Met Lys Val Tyr Val Asp Pro Ile Thr Tyr Trp Lys Asp
            100                 105                 110

Gly Tyr Asn Ile Leu Asp Val Ile Ile Leu Ile Ile Leu Thr Ile Pro
        115                 120                 125

Tyr Leu Leu Arg Lys Ile Lys Gly Asn His Ser Ala Tyr Leu His Phe
    130                 135                 140

Ala Asp Gly Ile Gln Ser Leu Arg Ile Leu Lys Leu Ile Ser Tyr Ser
145                 150                 155                 160

Arg Gly Ile Arg Thr Leu Ile Ile Ala Val Gly Glu Thr Val Tyr Thr
                165                 170                 175

Val Ala Ser Val Leu Thr Leu Leu Phe Leu Leu Met Phe Val Phe Ala
            180                 185                 190

Ile Leu Gly Phe Cys Leu Phe Gly Val Thr Asp Arg Gly Asp Leu Glu
```

```
            195                 200                 205
Asn Trp Gly Asn Leu Ala Ser Ala Phe Phe Thr Leu Phe Ser Leu Ala
    210                 215                 220
Thr Val Asp Gly Trp Thr Asp Leu Gln Glu Glu Leu Asp Lys Arg Lys
225                 230                 235                 240
Phe Thr Val Ser Arg Ala Phe Thr Ile Leu Phe Ile Leu Leu Ala Ser
                245                 250                 255
Phe Ile Phe Leu Asn Met Phe Val Gly Val Met Ile Met His Thr Glu
            260                 265                 270
Asp Ser Met Lys Lys Phe Glu Arg Asp Leu Thr Leu Glu Arg Asn Leu
        275                 280                 285
Ala Ile Met Glu Glu Lys Gln Ile Ile Leu Lys Arg Gln Gln Glu Glu
    290                 295                 300
Val Asn Arg Leu Met Asn Thr Gln Lys Thr Gly Ser Met Asn Phe Ile
305                 310                 315                 320
Asp Met Val Glu Gly Phe Lys Lys Thr Leu Arg His Thr Asp Pro Met
                325                 330                 335
Val Leu Asp Asp Phe Ser Thr Ser Leu Ser Phe Ile Asp Ile Tyr Leu
            340                 345                 350
Val Thr Leu Asp Asn Gln Asp Val Ile Val Ser Lys Leu Gln Glu Leu
        355                 360                 365
Tyr Cys Glu Ile Val Asn Val Leu Ser Leu Met Leu Glu Asp Met Pro
    370                 375                 380
Lys Glu Ser Ser Ser Ser Leu Ser Gly Leu Ser
385                 390                 395

<210> SEQ ID NO 5
<211> LENGTH: 6358
<212> TYPE: DNA
<213> ORGANISM: Homo sapiens

<400> SEQUENCE: 5
acaggcatga gccaccgcgc ttggccagaa gtggcattct taaattcaag aaattgggat      60
ggggagtatt cacacatttt ataacccaga aattcaagca attctggtga ctacaaatgc     120
attgttttgg agaatagttg taaggtggaa aaagaattag gaactcgaca gatagtgagt     180
tttaacttta ataacaatt cttctttttgt tttgttttgt ttgagacggg gtctcgctct     240
gctgcccagg ctggagtgca gtggcaggat cacggtttat tgcagcctta acctcctggg     300
ctcaagcagt tctccctcct cagcctccag agtagctggg actataggca agtgccacca     360
cgcctgacta atttttaaat ttttgtaga gatggggtct cccatcttgc ccaggctggc     420
cttgaactct tgggctcaag caagcctccc acctctgcct cccaaagtcc aaggattaca     480
ggtgtgagcc attgcccca gccagtataa cagtttgtgt gtgtgtgtgt gtgtgtgtgt     540
gtgtgtgtgt gtttgacacg gggtctcatt ctgttgccca gcagtagtg tagtggtgcg     600
accatggctc actgtagtct tgacttctca ggctcaagtg atcctctcac ctcagcctcc     660
tgagtagcag cggttacagg catgcatcac cacacctggc ttatttttaa aacttttttg     720
tggagacagg gtcttactat gttgccatgg ctggtctaga acttctgggc tcgagtaatc     780
ctcctgcctt ggcctctcaa aatgttggga ttacaggtgt gagccactgt gtcataacaa     840
ttatttttaaa attttatttt atttatttt aataattata caagatggag tctcactatg     900
ttgcccaggc tggtcttgaa tgcctgggct caaatgatct tcctgccttg accccccaaa     960
gtgctgggat tacaggcgtg agccactgcg cctggcctat aacaattctt atgaagctaa    1020
```

```
agttgatttg gatttagct gccgttacta cttatataat taattagatt aaacaagtca    1080
caaaaattgg atgagctatc ttggtgtgtt ttctttactt ttctctttca acagagagtt    1140
gaaggagagg acaagtgtct tgtctgtggc ttccaggaat gtgtggcaat ataagattta    1200
ctgttacagc agccaactca ccaagtcatt atttgactta ctgagttaag gaggaactaa    1260
gggtcatttt ccccccatca tttgcatgtt ttgactcctg aactgagggt ctacggccac    1320
tgaagctaga agctagaagg gtgttaatca gtagtgagct ctacttactc catgtgtcac    1380
tgacagatgt aaaaaggaat atcaagtaat ctattattta aaaattgtaa taagagtgtt    1440
ttttgaagga attcaggaat gtactactaa cgagattatg atgcaggtat atccatccat    1500
gaagcatttg ttagtcccct gaagcatcat ggtagtggaa tttaacatgg atcatctttg    1560
taaacccacc tctctttagg ggccagagaa atcactgttt gttacaacaa gcaaaccttt    1620
ccctctccat gtcacccttg ccccaaacct gagaaacata tgggaacatg gcacagaggc    1680
tgagctctct gaagccagtt cctggctggt tttgctggcc agggagaggc aggtgtggtc    1740
agttgccctg tggacatgtg gtgtgcaggg agagaagagg gaaagagcc actcaggctc     1800 tctggctgcc aggggatcca gactcttagc actagaactt ctgtttctta gaattcttcc    1860
caaggaaaag acaaaactgt gtttttataa gctggtttcc tatagtgtag atttgggact    1920
tttatacatt ttattaccaa atatttttag ttaagtgctt caattttcaa cattaattct    1980
ttaaaatttt cttttgagaa tcatcacctg gatttacatg aattttttaa gcatgaaaaa    2040
atttaaacat attcaaaagt acatgaatag tacattgaag ccttatatac atatcaccca    2100
gatataaaaa ttaccaagat tttgtcccag ttgcttcatt ttccctgttt ccttctttgc    2160
taaagtattt aaaagcaaat cccagatagc ttatcatttc acccctatat ccttcagtaa    2220
gtttctatgg aaaatatggc cattttcttg tataaaccac agtacctctg ttttttttt     2280 ttgagataga gtctcacact gtcgcccagg ctggagtgca atggcgtgat cttggctcac    2340
tgcaacctct gcctcccagg ttcaggcgat tctcctgcct cagcccccg ggtagctggg      2400 attacaggtg tgcgccacca tgcccagcta atttttttt gtatcttcag tagagatggg     2460
gtttcaccat gttggccagg ctggtctcga gctcctgacc tcgtgatcgc ccgcttaggc    2520
ctcccaaagt gctgggatta taggcataag ccacagcgcc cggcccacag taccatttt    2580 atacctaaca aagtgattcc ttggtacact taatacctag gcaaaatcaa attgtcctga    2640
aggtcatgaa tgtccttgga cagtaatctg gttctaatcg aggatctata tgaagcccac    2700
caatcgcatc tggttgttgt gtctctttag tctgtcagtc tggagcaagc tcccctccct    2760
tcctcagttc cccatgttat ttatttattg taaaaactgg gtcagttgtg ctgtagaata    2820
ttctgctttc tggatttgtt tgtttcttcc tgtggtgtca tttaacttgt tttactatac    2880
cctaaacgga acccttttcc tctgttttca gcagaagtct gagaggctaa acttgatggc    2940
tgtgttaaca tatgtcacgt gtagcacagt ggagaaagca ggatatggct cataatgaca    3000
gtggtgaaga cctgcgaatg aagttgctag ttatcaccta cattagggtt tgacataggt    3060
ctatgttatg ggtcgctgca tctgctggaa ctcacagact ttactataga gaatcaaaga    3120
tcccgtatcc gaagtctatg gaaatgctca tggtggtaaa ttccaacaga atgaaacacc    3180
aaacttgctt aaagtaactc acgtttcaat ttgaaagaga tattgtcaaa attggaggcc    3240
cccaggttcc tgtctgttcc aaatctttgc atgatgacag tggtttctct gatgtggtaa    3300
gctttggctt tcttctgttt tctttctaaa agatcactgg agtagagagg agttaaacag    3360
```

```
acatgacctt tgacctcttg catgacctcc acagatagca aaccgggccg acacatggtt    3420
gacgatgtcc ttttctacaa tgaagttaat gaaagttctg aaaatagtga ttactttctg    3480
acattgatag gatttaggaa acctctggat aaatagctta agcatggctg tttatgtttt    3540
tgctatagac aaaaagcagc agcatgtaca ttgtatttgg acacaagcct gcctcggtta    3600
atatattgaa ctattggacc actagggtta gtagggagcg gtctgtacac tttctgattc    3660
agcattcaga acattctag  gtggactctg tagcttttcag ttttgtaaag ttatcagaaa    3720
aacatcggga gggtttggcc atcatatgtg agctttgtgt ttcaatgcca gttactcagg    3780
attagtaaat taatgactgt ccagaggact tcagggtcac caagctgctg cacctgccat    3840
tggctgactc tccccggcta tctgtggctg agatggtgct gcttaggtca cgcagagcat    3900
gagctgctgc tgaaagggca caggagatgg cccttgggct tctcatccca ggatgcctgc    3960
cctgcccacc aatccatgag aagatatgta tgatttcagt aggccctgga tcagcttgtc    4020
acctctggtt tcctgtttgc tttccactca ctcagctgga gtttcatttc cagactaaag    4080
tcttcatcat tggcttcaga aacagcattc atctgtggct gtgctgatgt agtacaccaa    4140
gaacaactgg gctcttctct gtcactttca gtgggctacc ttccctcacc tctccaagca    4200
gcatgaaaga attctttaca ttttttaatct ctttttttgtt tttccctgaa agtatgcttt    4260
ggtgcttaaa gagagaagtc acaaaagtat actactgagt ttcctggaga tgaaatcctg    4320
ttgtccctag ctatgtgaat gagcacaggg atccctgatg ccattatttt gtatattcat    4380
acggcacaca cttactgagg gccttctgtg tgccctaggg gattgagcac agtgacatat    4440
cagggcaggt agaaacagat ggagagctga tgcgggctgt cttagagcag ctgccccagg    4500
aggcccctgt ggatggatgt tgggcaggag ccctgagacg ttagggggcat ataactaaag    4560 gacatagcag gagttatagg aggagctgat ccctgaggga aacaatgaag acggagaaga    4620
tggggctaaa gtttgaattg tggggacatt aatcacagtg attcttaaaa ctttgctgtt    4680
gatgatttta aatggagaaa atgagtacgt aagatgttat ttcccagttc agtatattgg    4740
ttgcccacaa agtatttttcc taccatgaat ggtcatatat acttgttgta gaataccagg    4800
gacagcagag atggtgggggt agttacttcc ttttcttaca gcccaagaac tttggtgtcc    4860
aggagattga ccaatttagc cactgagcat ttaatacaac acagggctac ccagatccca    4920
ctgtcctgat ttgccctgaa agccaaagga gttaggagaa ggtgagtggg gagaatatat    4980
taatcctgag agttgaacag agcaaaaatc cctattactt ttgtacttaa aacatctctg    5040
ccacatgtgc tcactctttta tattctgttt aggtggttta tatgtgcaca tcccatccta    5100
tgcctgcagt tagccaactc agggtttata ttgcctcctt tcttttttttc tttttttttt    5160 tttttttaag agatgggtc  tcattctatc atgcagactg gagtgcagtg gtgtgatcac    5220
agctcattgt aacctccaac gcctggacta aagtgatcct cctaccttgg cctctctggt    5280
agctgggact acaggtgcat gccaccacac ccacctaatt ttttttattt ttatttttttg    5340 tagagacagt ctcactatct tgctcaggct agtcctgaac tcctgggctc aagttatctt    5400
gctgcctcag cctcccatgg gtaattttta tttccttttt tttttttttttt ggagatggag    5460 tttcgctctt gtcgcccagg ctggagtgca atggcacgat cttggctcac tgcagtctcc    5520
acctcctggg ttcaagtgat tctccatcct cagcctcctg agtagctgag attacaggca    5580
actgccacca tgcgcggcta atttatgtat ttttttttag taagagatgg ggtttcacca    5640
tgttggccag actagtctta aactcctgac ctcaagcgac ctgcctgcct tggcctccca    5700
aagtgctggg attacaggca tgagccgcta tgcctcgtcg ctgattttta tttcttattt    5760
```

-continued

```
ttttttttaga gatggggggtc tcactatgtt gctcaggctg atctcaaact cctggcctca      5820
agtgatcctc ccaccttagc ctcccaagtt gctgggatta taagtgtgag ccactatccc      5880
tacctcacta ttaccttctt tgcttctctt gttttctttt gttctaagtc aaacccatca      5940
caatcttttc ttgtccttcc aggtgttttc cagtgctgtg ccctggatgt gctctctttc      6000
tcttagagcc cagagaactt gcttttcccc cttatatatg acccttaact ttttctaaca      6060
cattattaag ggcctgtgtc tatcagctgg gggcacttct tgaagggagg gcctttgtgt      6120
ggtctgtttc tagtgacttc cagctttaac ccagagcctc atgattgctg ggtgcccata      6180 gccttttttgc tgaatggagg cactcagtct ccttgggaag agagaatcca tgatagaccc      6240
acttgggagc tccccacttc aggggcctac acactggtaa tgcaacagaa tgcccaagag      6300
tgacctcata aagcaaggat tcccttcgtg gccccttctc tgctgcctct cagaatcc       6358
```

<210> SEQ ID NO 6
<211> LENGTH: 78
<212> TYPE: DNA
<213> ORGANISM: Homo sapiens

<400> SEQUENCE: 6

```
agacgctaag gaaaatccct aagcagagat tttctgttgg atgctaaaag caaggaataa        60
aagttgaaaa tttggaaa                                                      78
```

<210> SEQ ID NO 7
<211> LENGTH: 72
<212> TYPE: DNA
<213> ORGANISM: Homo sapiens

<400> SEQUENCE: 7

```
ctgggcatgg ggcacccatg tgccgagagc cttgcagacc atgacaggtc cctattaaac        60
acaggctttc tg                                                            72
```